(12) United States Patent
Chernyak

(10) Patent No.: US 9,345,645 B1
(45) Date of Patent: May 24, 2016

(54) BI-DIRECTIONAL ADAPTIVE DRUG DISPENSER FOR MANAGING DIVERGENCE BETWEEN PRE-SET REGIMEN AND ACTUAL PERFORMANCE

(71) Applicant: Alex H. Chernyak, San Francisco, CA (US)

(72) Inventor: Alex H. Chernyak, San Francisco, CA (US)

(*) Notice: Subject to any disclaimer, the term of this patent is extended or adjusted under 35 U.S.C. 154(b) by 0 days.

(21) Appl. No.: 14/545,200

(22) Filed: Apr. 7, 2015

(51) Int. Cl.
| | |
|---|---|
| G08B 1/00 | (2006.01) |
| A61J 7/04 | (2006.01) |
| A61J 7/00 | (2006.01) |
| B65D 83/04 | (2006.01) |
| G06F 19/00 | (2011.01) |

(52) U.S. Cl.
CPC .............. *A61J 7/0481* (2013.01); *A61J 7/0076* (2013.01); *A61J 7/0418* (2015.05); *A61J 7/0427* (2015.05); *B65D 83/04* (2013.01); *G06F 19/3462* (2013.01)

(58) Field of Classification Search
CPC ..... A61J 7/0481; A61J 7/0418; A61J 7/0427; A61J 7/0076
USPC ..................................................... 340/309.16
See application file for complete search history.

(56) References Cited

U.S. PATENT DOCUMENTS

| | | | |
|---|---|---|---|
| 5,915,558 A | 6/1999 | Girvetz | |
| 6,256,967 B1* | 7/2001 | Hebron | B65B 57/20 53/131.3 |
| 6,604,650 B2 | 8/2003 | Sagar | |
| 6,779,663 B1 | 8/2004 | Pocsi | |
| 7,081,807 B2 | 7/2006 | Lai | |
| 7,269,476 B2 | 9/2007 | Ratnakar | |
| 7,359,765 B2 | 4/2008 | Varvarelis et al. | |
| 7,382,692 B1* | 6/2008 | Hildebrandt | A61J 7/0472 200/572 |
| 7,395,214 B2 | 7/2008 | Shillingburg | |
| 7,414,534 B1* | 8/2008 | Kroll | A61B 5/0031 128/903 |
| 7,554,434 B1* | 6/2009 | Gifford | A61J 7/0409 215/230 |
| 7,735,684 B2* | 6/2010 | Coe | B65D 83/0409 221/25 |
| 7,877,268 B2 | 1/2011 | Kulkarni | |
| 7,896,192 B2 | 3/2011 | Conley | |
| 7,907,477 B2 | 3/2011 | Puzia | |
| 7,978,564 B2* | 7/2011 | De La Huerga | A61M 5/14212 221/15 |
| 7,993,055 B2 | 8/2011 | Nurse | |
| 8,026,796 B2* | 9/2011 | Kiran | A61J 7/0472 340/309.16 |
| 8,060,249 B2 | 11/2011 | Bear et al. | |
| 8,068,931 B2 | 11/2011 | Tran et al. | |
| 8,069,056 B2 | 11/2011 | Walker et al. | |
| 8,102,735 B2* | 1/2012 | Morse | A61J 7/0472 221/2 |
| 8,269,613 B2 | 9/2012 | Lazar | |
| 8,284,068 B2 | 10/2012 | Johnson | |
| 8,319,613 B2* | 11/2012 | Lazar | A61J 1/14 340/309.16 |
| 8,348,093 B2* | 1/2013 | Jeyarajan | B65D 83/00 221/15 |
| 8,485,359 B2* | 7/2013 | Anderson | B65D 1/2807 206/219 |
| 8,538,775 B2 | 9/2013 | Skomra | |
| 8,727,180 B2* | 5/2014 | Zonana | B65D 83/0409 221/195 |

(Continued)

OTHER PUBLICATIONS

US 8,754,659, 8/2013, (withdrawn).

*Primary Examiner* — Hai Phan
*Assistant Examiner* — Zhen Y Wu

(57) ABSTRACT

A medication dispenser for coordinating the treatment plan and treatment regimen for a medication (what medication(s), what dosage(s), what time(s), what interval(s)), that presumes errors, emergencies, and changes will happen and must be handled; and so rather than seeking perfect compliance at every level of provisioning, handling, and taking of the medication, examines and as possible corrects and then records as correct or deviating, actual use, and so tracks the experienced regimen.

19 Claims, 14 Drawing Sheets

(56) References Cited

U.S. PATENT DOCUMENTS

| | | |
|---|---|---|
| 8,727,189 B2 | 5/2014 | Zonana et al. |
| 8,727,208 B2 | 5/2014 | Poisner |
| 8,754,769 B2 | 6/2014 | Stein et al. |
| 8,781,856 B2 | 7/2014 | Hanina et al. |
| 8,963,710 B2 * | 2/2015 | Huang ............... A61J 1/03 340/309.16 |
| 2001/0028308 A1 * | 10/2001 | De La Huerga .. A61M 5/14212 340/573.1 |
| 2004/0065053 A1 * | 4/2004 | Rice .................. B65B 5/103 53/445 |
| 2006/0102649 A1 | 5/2006 | Garukyan |
| 2009/0009332 A1 * | 1/2009 | Nunez ............... A01K 11/007 340/572.1 |
| 2010/0142330 A1 | 6/2010 | Reygaert |
| 2010/0169111 A1 * | 7/2010 | Brue .................. G06Q 50/22 705/2 |
| 2010/0270257 A1 * | 10/2010 | Wachman ........... G06Q 10/10 215/228 |
| 2011/0022224 A1 * | 1/2011 | Park .................. A61J 7/0409 700/232 |
| 2014/0240094 A1 | 8/2014 | Stein et al. |

\* cited by examiner

BI-DIRECTIONAL ADAPTIVE DRUG DISPENSER FOR MANAGING DIVERGENCE BETWEEN PRE-SET REGIMEN AND ACTUAL PERFORMANCE

CROSS-REFERENCES

None

GOVERNMENT RIGHTS

None

BACKGROUND OF THE INVENTION

1.A. Field of the Invention

In the $20^{th}$ century, medication principally addressed illness which was 'incident', i.e. relating to an injury, an infection, or an infestation; and the best health results came from public health efforts (safe water, personal hygiene, vaccinations). Across the globe the average lifespan surged upwards, in some places at more than a year's gain for each year of progress. These now are seen as "easy victories" over the most broadly-shared killer ills; for in the $21^{st}$ century people remain mortal and health care's share of our national GNP has more than doubled.

This century starts with an estimate that in the United States alone 133 million people suffer from at least one chronic illness, and the reality that chronic illnesses lead to approximately seven out of every ten deaths in the United States each year. Medications often prescribed to alleviate and treat these chronic illnesses fail principally because current levels of adherence to medication regimens are at or below 50%. Patients, even those with access to preventative or palliative medications, are not properly treating their chronic diseases, this century's major killers.

Taking medication sounds simple in theory. As with most of life, reality presents a host of complications. For all that there are standard and approved regimens, reality includes transient, temporary, interruptions; context-specific deviations; emergency changes; and always purely 'human', but reality-based, differences between the theoretical (standard) ideal and the pragmatic real-time and real-world experience(s). For and as part of each specific, prescribed regimen, each human being experiences and causes divergences between his or her planned, or prescribed, dosage and the reality of what doses (and when) he or she actually takes.

A patient may have difficulty remembering to take his medicine at the recommended time(s). Or a patient may have difficulty remembering that she has already taken a dose. Some patients have difficulty remembering the recommended dose of medicine, especially if that dose requires more than one unit (pill) of the same medicine. The reality is even more convoluted for any multiple drug regimen, and one mistake may pose grave consequences to the patient. These problems both especially true and may compound for patients (like elderly, disabled and cognitively impaired individuals, or patients with psychiatric disorders) with inadequate skills or knowledge to follow a medicine regimen, and those facing a language barrier. An increasing segment of the population joins those most vulnerable as their regimens individually comprise multiple medicines, each with a different schedule and instructions.

As eyesight fades with age reading labels of medicine containers can present a problem. Even young, alert patients can be overwhelmed by life, work, family and other responsibilities and forget to take their medicines. This is especially apparent with temporary treatments (e.g. antibiotics), when the medicine is taken for a period of time too short to generate a routine.

Then add to all of the above rapid changes in the selection of formulary (and thus features of the actual pills), packaging errors, and intentional or inadvertent switching of medications amongst containers, that lead to divergences between what is thought to be in a container and what is actually dispersed at the time of use. The end result is too often that the amount of medicine actually taken is too low to affect the treatment, or so high as to cause an overdose, or that the wrong medication entirely is taken.

Patient compliance with medication dosing schedules is a serious problem. Approximately 60% of prescribed medication is not taken as directed. Non-compliance leads to worsening illness, hospitalization, irreversible loss of function, and death, resulting in tremendous human and financial costs. When medicines are dispensed, especially outside hospitals, errors in selection of the correct pill and the appropriate dose add further morbidity and mortality.

For example, elderly patients and patients taking multiple medications at different dosing schedules may have difficulty remembering to take their medications at the scheduled times. Approximately 90% of elderly patients make medication errors, 35% of which are serious. Approximately 40% of all hospital admissions among elderly patients are due to medication problems.

The gold standard remains supervised administration of each dose of each medication and of the integrated medical regimen by a highly-educated professional (doctor, nurse, pharmacist, or other medical specialist); but for most situations this is costly overkill. Even though medical professionals on average do worse than the medial performance attainable with automatic support systems, whether such be as simple as a checklist (Atul Gawande) or as complex as an advanced medical robot (Intuitive Surgical's da Vinci machines).

The current state of the art has many methods and systems seeking to effect proper medication by individuals, because such actions are important—sometimes literally vital—in preventing sickness, complications, and even death. Many machines and methods have been proscribed, prescribed, and even patented in this field.

Giving instructions and then letting patients fend for themselves has been shown not to work particularly well. For improper taking of medicines only is not the greatest medical danger. Rather, it is any unsensed or untracked divergence between medical presumption and real-time performance, which gives rise to improper feedback, which then leads to the physician concluding that it is the medicine and not the actual regimen that is failing—which then causes the physician to change the wrong factor (dose, timing, or even choice of drug) in a mistaken effort that fixes the wrong problem. These divergences can be frustrating to both patient and physician, detrimental to the experienced care for the chronic illness, and increase costs for no gain; yet be simply and readily correctible or handleable within an existing treatment regimen when truthfully managed.

1.B. Description of the Related Art

A number of systems and devices already exist that provide instructions, alarms, or assistance to a user regarding when to take at least one medication, and/or to record its having been taken. These include ordinary pen, paper, Post-It® notes, and refrigerator-front reminder magnets. All incorporate one fundamental defect: they presume a perfect linear progression from alert to event, and thus diverge from reality whenever the user's actual behavior does not match the preconceived and pre-set process. Prior inventors defined their goal as trying to meet "The need for a device that will automatically dispense the proper pill(s) in the proper amount(s) at the proper time(s) each day and alert the user of the devise to take the dispensed pills . . . . " (U.S. Pat. No. 8,068,931, "Systems and Methods for Monitoring Pill Taking", Tran, A. A. A. et al., issued Nov. 29, 2011, Col. 1, lines 18-21).

Thus the prior art is rife with simplifying, perfectionist, and unrealistic presumptions. Most share that of U.S. Pat. No. 5,915,558, "Portable Pill Box With Alarm", Girvetz. N., issued Jun. 29, 1999, which is substantially as its title describes. This invention presumptively links opening the access door to the storage area with correctly taking the content(s) therein: "If the pills are accessed (door 40 is opened and/or a vial is removed), then the acknowledge signal will indicate that the contents of the pill box have been accessed in response to the alarm signal." (Col. 5, lines 51-54) The contents, number of units (pills) taken, and even presence of the 'vial', are all presumed correct; and "access" is presumed to be flawlessly linked to ingestion.

U.S. Pat. No. 6,604,650, "Bottle-Cap Medication Reminder And Overdose Safeguard", Sagar, R. B., issued Aug. 12, 2003, also presumptively links opening the cap with taking the content(s) therein: "The cap would use the time it was last removed (as detected by the sensor) as the datum for the Time since last dose." (Col. 4, lines 64-65)

U.S. Pat. No. 6,779,663, "System and Method for Loading Pills Into A Pillbox", Pocsi, J. P., issued Aug. 24, 2004, is aimed at the pharmacist and/or her assistant, or the persons providing the medication, rather than those taking it—or more specifically, at the steps of preparing a medicine dispenser for future use, rather than at the point-and-time of use for specific and particular dose(s). This invention's core "latticework pattern of rows and columns" (Col. 3 lines 18-19) and "loader form" (Col. 12, line 8) are not any part of the present invention.

U.S. Pat. No. 7,081,807, "Automatic Pill Reminder Bottles", Lai, J., issued Jul. 25, 2006, concedes that it is merely "a reminder device to remind user to take pill regularly" [sic] (Col. 1, lines 46-47). As with Sagar/U.S. Pat. No. 6,604,650, it links the opening and closing of the bottle to the presumptive taking of the correct dose.

U.S. Pat. No. 7,269,476, "Smart Medicine Container", Ratnakar, Nitesh, issued Sep. 11, 2007, presumptively links dispensation of the medication with its being correctly taken; and further depends on the correct 'bulk' medication being loaded into the container in the first place (Col. 15, line 21) and not broken or disturbed before or upon dispensation. As with the preceding patents, "The time of opening of the outlet door (22) is recorded as 'consumption time' by the sensor (23) . . . . " (Col. 10, lines 27-38) This patent is advanced over the earlier ones, for it contains a sensor in the dispensation channel to count each pill that is dispensed (Col. 14, line 58), and a second sensor in the outlet transition (Col. 15, lines 1-4); thus it does not presume that the right number have been removed when the timer is activated and the door opened.

U.S. Pat. No. 7,395,214, "Apparatus, Device and Method for Prescribing, Administering and Monitoring a Treatment Regimen For a Patient", Shillingburg, C., issued Jul. 1, 2008, describes such a device and approach eminently well; its system and device provides instruction to a patient regarding the medications to be taken. Furthermore, the system supposedly may determine whether a specific prescription is appropriate given the patient's conditions and other medications he or she may already be taking. That system also supposedly may monitor compliance of the patient with such a regimen through its dispensing of medicine in accordance with a predetermined treatment protocol. While that system offers improvements over 'prescribe and pray' approach, it presumes perfection in use and operation, for that system provides no mechanism for actually confirming that a patient is in fact ingesting or otherwise properly administering required medication, which it presumptively links to the dispenser being opened. As itself states:

"the Device enables the Doctor . . . to verify that the patient actually opened the Device (and presumptively took a pill) . . . " (Col. 13, lines 20-22; emphasis added)

That invention may be sufficient for one who is in full possession of their mental faculties; but not help any individual who may have difficulty following directions, or one who is actively avoiding medication; either may still not be taking required medication after it is dispensed. Furthermore, it requires preloading of various medications into a dispenser and has no function to check whether the medication which is actually dispensed is that which is intended; so if there is any error in the loading, this invention has no way to detect (and thus correct) it at the time a dose is dispensed. While this patent does suggest that "each of the chambers 370 may be uniquely configured (based on the size and configuration of a given medication) to filter pills through the device and into the patient accessible chamber 378" (Col. 19, lines 63-66), or an alternative having "customized sleeves that are inserted into the chambers" (Col. 19, line 1; FIG. 3H, 3I), even if an administering manager regularly visits to ensure appropriate medications are loaded, it is surely possible that an inexperienced or momentarily inattentive loader may place incorrect medications into the device (or chamber), or may somehow provide incorrect dosages into the device. It has no test for mis-loaded and thus mis-dispensed medications. It uses "as a medication transferring device, a slide tray 380" (Col. 19, lines 4-5).

Finally, not only does this invention's description openly state its presumption that each time a pill is taken out it is (a) at the time, correctly being removed, and (b) taken; it lacks any check on whether the count of pills taken out was correct, or means to either replace the pill or to account for it not being taken (and thus any ability to reverse the presumption of perfect compliance based on reality experienced by the user).

U.S. Pat. No. 7,359,765, "Electronic Pill Dispenser", Varvarelis, N. M. et al., issued Apr. 15, 2008, also depends on the correct medication being loaded in the first place into its " . . . receptacle for storing and dispensing any size of pill P . . . " (Col. 4, line 34). It (as with the cited prior art) fails to check whether what is being dispensed is a pill P, or a pea, or a stone, or a pill not-P.

U.S. Pat. No. 7,877,268, "Intelligent Pill Box", Kulkarni, A. U., issued Jan. 25, 2011, links removal of an individual pill container with the taking of the correct dosage of that medication (though with flawed English from a pro se applicant):

"If the pill box is lifted after this signal then the green flashing LED will glow continuously green with no beep sound. (This will indicate that the person is taking the pill)." [Sic] (Col. 6, lines 59-62)

"But if the person keeps back the vial within 20 sec. then Smart-Pill-Box assumes that the pill has not been consumed." [Sic] (Col. 6, line 66-Col. 7, line 1)

"If the person keeps the vial back after 20 sec. Smart-Pill-Box records that the pill has been consumed and sends the data to server through telephone line." [Sic] (Col. 7, lines 3-5)

Although this patent's specification asserts that the device weighs the contents of the pill box (Col. 6, lines 13-18), examination of the claims, and perusal of the image file wrapper, disclose this aspect was not asserted during the prosecution of the patent, and further disclose that the examiner's allowance was predicated solely on the timing intervals relating to the removal and replacement of the pillbox within the device as part of its "Dispensing Scheme" (Col. 6, line 55-Col. 7, line 13). The specification fails to provide any operative instruction sufficient to meet a 35 U.S.C. §112 'enablement' requirement as to how the device effects this functionality.

U.S. Pat. No. 7,896,192, "Patient-Controlled Timed Medication Dispenser", Conley, N. S. et al., issued Mar. 1, 2011, addressed the need for medication which may not be delivered at a pre-fixed schedule but instead may have a first dose delivered at a time of the patient's selection, yet which prohibits access to a further dose until a minimum time interval has elapsed. The device also controls access through an authentication operation, and stores a record of its operation. The invention presumes that presentation of the medication in an 'open' container is equated with the patient taking the medication, even though it limits the presentation time preferentially to less than half a minute. (Col. 11, lines 27-30) The passage of time alone—not whether any medication is removed—is used to establish that a dose was taken. (Col. 11, lines 30-35) This lack of feedback means that half of the potential dose-carrying sites are empty. (Col. 11, lines 49-51; Col. 12, lines 10-12, 65-67) Should the patient not meet the window of opportunity and take the dose when presented, the invention presumes that all of the minimum necessary interval must first pass—"if . . . the dose is not removed from the retention area", except that "the patient can request a dose from the attendant". (Col. 14, lines 25-27; lines 27-28) The literal blindness of this patent to alternative approaches can be seen in its provision for a sensor (Col. 15, line 25) that is only used to determine whether a medication area is properly aligned (Col. 15, lines 31-34), and not whether any medication is in the medication area. Later, however, while it describes a 'dose presence detector 757' (Col. 19, line 39), this is its only mention—no use or connection exists elsewhere in the Specification. This detector only functions to detect removal—not the presence, or introduction—of a dose (Col. 19, lines 50-52) and is not mentioned in any of the claims.

U.S. Pat. No. 7,907,477, "Bottle Cap Medication Timer", Puzia, Scott; issued Mar. 15, 2011, comprises solely a "disposable electronic timer" (Abstract, line 1) which has timer-setting and control buttons, only.

U.S. Pat. No. 7,993,055, "Method and Apparatus for Alerting A Person At Medicine Dosing Times", Nurse, C. L. et al., issued Aug. 9, 2011, chiefly differs from U.S. Pat. No. 7,907,477 by not being on the cap, secondarily by excluding any visual display, thirdly by allowing for 'creep time', and shares the presumptions that (1) opening the dispenser (switch) is equivalent to the dosage being properly taken (" . . . activating a switch when an annunciator is activated causes the dosing schedule to advance to the next dosing interval"; Col. 3, lines 42-44; FIG. 5B); and, (2) only the proper medication is in the container ("A method . . . comprises the steps of dispensing medicine into a container . . . . "; Col. 3, lines 60-61).

U.S. Pat. No. 8,060,249, "Medication Dispenser With Integrated Monitoring System", Bear, D. M. et al., issued Nov. 15, 2011, requires all of "a plurality of storage compartments" (Col. 1, lines 49-50), "an image capturing device" that sees into each storage compartment (Col. 1, lines 52-54, FIG. 2) and a separate and remote "central monitoring system" to which the device transmits its images (Col. 1, line 56, FIG. 4; Col. 15, lines 26-29; Col. 16, lines 18-20). This invention depends on ensuring compliance through live (albeit remote) observation by human monitors (Col. 5, lines 6-8; Col. 7, lines 19-25; Col. 9, lines 14-17; Col. 13, lines 19-22).

U.S. Pat. No. 8,068,931, "Systems and Methods for Monitoring Pill Taking", Tran, A. A. A. et al., issued Nov. 29, 2011, also presumptively links the opening of a compartment with the medication(s) within being taken. (Col. 6, lines 39-46; FIGS. 5, 6) The leaps of presumption go further, as the inventors assert that if taken "around normal lunch time when the medication should have been taken on an empty stomach, the system provides a warning and reports the event" (Col. 2, lines 54-56); and initially assume that "multiple compartment openings during one medication dispensing event" leads to a mistaken taking, instead of checking whether the user merely inadvertently opened the wrong compartment without removing anything (Col. 3, lines 17-19). Even for the further embodiment when the weight is directly measured, "the system infers that the pills have been removed and (presumably) taken by the patient" (Col. 7, lines 9-10).

U.S. Pat. No. 8,069,056, "Methods And Apparatus For Increasing And/Or For Monitoring A Party's Compliance With A Schedule For Taking Medicines", Walker, J. S. et al., issued Nov. 29, 2011, requires a plurality of medicine containers which each contain different medications and wirelessly communicate (Col. 2, lines 56-61; Claim 1, Col. 36, lines 26-28). It also envisions an off-site, third-party "controller 106 may comprise, for example, a computers at an insurance company or medical facility, or . . . an authentication server . . . . " (Col. 9, lines 55-57). This invention presumes that proximity between the two containers equals compliance (Col. 11, lines 44-46; Col. 16, lines 29-34 and lines 63-67; and particularly, Col. 17, lines 61-63: " . . . that identify compliance/proximity information regarding the taking of the medicine . . . "; Col. 21, lines 27-29); though it does include as alternative embodiments allow additionally the use of any of a pressure, weight, or RFID sensors as "any attribute that indicates the patient 104 has complied . . . " (Col. 24, lines 18-41; Claims 7 & 8, Col. 37, lines 5-10).

U.S. Pat. No. 8,284,068, "Activity Monitor To Alleviate Controlled Substance Abuse", Johnson, S., issued Oct. 9, 2012, focuses on detecting, collecting, and storing information about when a container "has been moved, opened or otherwise tampered with" (Col. 2, lines 5-6). This invention also presumes that moving or opening a container means that the contents within have been taken (Col. 10, lines 47-50). This invention does consider at least the possibility of feedback, but presumptively associates this as "in response to feedback from other sources . . . " (Col. 11, lines 16-17).

U.S. Pat. No. 8,269,613, "Smart Cap for a Medicine Container To Dispense A Medication While Self-Verifying Medicine Identity", Lazar, Steven S., issued Sep. 18, 2012, begins with identifying, discussing, and revealing a few of the limitations of the art prior to its filing. This patent comes closer than some of the others, but presumptively links dispensing the medication with its being taken, without considering the potential that the medication (all or part of the dose) may need to be returned when the patient cannot or should not take it; for the invention in this patent is "to prevent the improper dispensing of the medication" (Col. 4, lines 53-54).

U.S. Pat. No. 8,319,613, "Smart Cap With Communication Function", Lazar, Steven, issued Nov. 27, 2012, (and a continuation-in-part of U.S. Pat. No. 8,269,613), also shares the presumptive linkage between the dispensing of a medication (correctly) and its being taken (Col. 2, lines 46-48; Claim 1, Col. 9 lines 54-59).

U.S. Pat. No. 8,538,775 (application Ser. No. 11/839,723, issued Sep. 17, 2013), Skomra, S. A., "Mobile Wireless Medication Management System" provides a medication management system employing mobile devices and an imaging technology so that a user is able to show a pill to be taken to the system, and the system can then identify the medication. Patient histories are available to an administrator, including various vital signs as measured by the system. Images may also be taken of the patient, provider, medication container or the like. While the system professes to ensure adherence to a protocol, the system only provides such help if requested by a user. There is in fact no particular manner in which to ensure actual adherence or the relationship of adherence to the efficacy of the drug over time. When customizing a medication regimen or monitoring a personal medication regimen, this is particularly relevant.

U.S. Pat. No. 8,727,180, "Smart Cap System", Zonana, M. et al., issued May 20, 2014, focuses on the dispensing aspect to enable accurate dispensing of a specific medication dose through a mechanically complex cap mechanism (FIG. 1-11, 13-23). This patent at least contemplated the possibility that an error may follow the dispensation of the dose:

"Thus, if the patient accidentally loses the medication as by dropping it down the drain, etc., and the patient urgently needs to access the medication, the patient may have not choice but to break the seal between the bottle 110 and the device 100 as by pulling the pull tab 1502 of the emergency tab 1500. However, when the patient returns to consultation with the physician and/or seeks refill, it will be immediately evident that the emergency tab 1500 has been removed and this will spur questions and require explanation." (Col. 12, line 62-Col. 13, line 3)

In short, that invention's solution to the problem of any post-dispensing error breaks the mechanism and allows no corrective feedback save through an external agent.

U.S. Pat. No. 8,727,208, "Method For Identifying Pills Via An Optical Device", Poisner, D., issued May 20, 2014, focuses solely on the problem of correctly identifying via an optical device (camera), what medication (composition and dosage) is in an unknown pill, chiefly for the use of emergency and law enforcement personnel and entities (Col. 1, lines 20-34; Col. 7, lines 27-30), instead of chemical analysis; and is not intended to be used by consumers or users of any pill(s).

U.S. Pat. No. 8,754,769, "Systems and Methods for Determining Container Contents, Locations, and Surroundings", Adhere Tech Inc., et al., issued Jun. 17, 2014, focuses on the specific aspects of using capacitance sensors for sensing the contents of a medication container (Col. 1, lines 21-23). Here, again, the presumption is that removal is the only operative action: "whereby a patient who does not take medicine as expected is reminded (e.g., with different and/or multiple reminders/alerts) until he or she removes the appropriate amount of medication from medication container 102." (Col. 8, lines 50-54.) This patent does allow the alternative sensing of when a cap has been closed or opened (Col. 9, lines 24-27), then explicitly states its presumptive coupling, " . . . thus signaling that the patient might have just removed medication from the container" (Col. 9, lines 30-31). Then this patent allows that a measurement might test the first presumption (opening=removal) (Col. 9, lines 33-35), but does not consider whether the second presumptive linking of removal of the medication with the taking of a dose, other than as 'timing' or data communication issues. (Col. 9, lines 41-58.) Its only concept of "feedback" is for a "backend system 104" through purely symbolic communication, "(e.g., via text message, email, and/or telephone calls to patients)" (Col. 14, line 6-9).

U.S. Pat. No. 8,781,856, "Method And Apparatus For Verification Of Medication Administration Adherence", Hanina, A. et al., issued Jul. 15, 2014, requires, as the present application does not, both video capture equipment (Col. 2, lines 64-66) and a third-party remote comparative monitoring of activity of a medication's user to ensure proper compliance with a prescription regimen "to confirm that the medication is being actually and properly taken" (Col. 2, lines 66-67).

U.S. Pat. Appl. 2006/0102649, "Good Cup", Garukyan, G.; published May 18, 2006, filed Oct. 5, 2004; Application Ser. No. 10/957,902, is merely a device to make removal of a pill from a vial easier.

U.S. Pat. Appl. 2010/0142330, "Attachable Device for Pill Container", Reygaert, P.; published Jun. 10, 2010, filed Oct. 30, 2007; Application Ser. No. 12/514,026, is a variation on timer-based dispensing which presumptively links access to the contents with dispensing and taking of the medication (¶0012, lines 7-8 thereof; ¶0027).

U.S. Pat. Appl. 2010/0270257, "Medicine Bottle Cap With Electronic Embedded Curved Display", Wachman, J. S., et al.; published Oct. 28, 2012, filed Apr. 29, 2010; Application Ser. No. 12/770,436, shares the approach of the prior art, that what is needed is support to effect perfect compliance [¶¶0036-0045]. This system also specifically requires a multi-color LED [¶0064, Claim 1] Most importantly, It shares with the prior art the presumption that accessing the medication (opening the specific dispensing point) is equivalent to the medication's being taken:

"The system assumes that if the medicine container has been opened and then closed, that the medication was actually taken and that the dosage was correct. Preferably, the number of pills has to be accounted for upon setup. The known number is decremented by the dosage amount when the cap is opened." [¶0055]

U.S. Pat. Appl. 2014/0240094, "Systems And Method For Determining Container Contents, Locations, and Surroundings", AdhereTech Inc., et al.; published Aug. 28, 2014; filed May 8, 2014; Application Ser. No. 14/273,289, a continuation of U.S. Pat. No. 8,754,769, also focuses on "increasing patient adherence to medication regimes" [¶¶0004; 0029]. This application implements the concept mentioned (without enabling detail) in U.S. Pat. No. 7,877,268 and in the further embodiment of U.S. Pat. No. 8,068,931 [¶0005] for detecting a quantity removed . . . but does not use any deviation from dosage to trigger alternative pathways (emergency under- or overdose concerns, or changed interactions with other medications); its focus is on providing "one or more reminders and/or alerts to the patient to take medication" [¶0037, 10 lines up from bottom of paragraph; ¶0040, 6 lines in]. This application does recognize a single flaw of the prior art in presuming that operating a switch equates to taking a dose, by imposing a timing constraint of a required delay to "prevent container 102 from measuring, recording, and/or reporting back a measurement when a patient accidentally activates the switch (e.g. presses the switch with the patient's finger) before the patient has removed any medication" [¶0048, $2^{nd}$ column on page, 7 lines down]. Yet its focus relentlessly remains on providing alerts, rather than tracking and managing divergences between prescription regimen and real behavior. (Among other assumptions, this invention presumes the medication has both been correctly loaded and has not deteriorated in storage.)

None of these devices, methods, systems, or prior art inventions fully address the underlying, fundamental problem which separates perfection (or prescription) from performance (reality). The fundamental problem which they do not consider nor address, is neither new, nor can it be solved by the most ingenious, thorough, imaginative, or intrusive alerts, buzzers, timers, reminders, or nagging. It is an old and well-known problem which defeats those more intelligent even more readily than it does those who are less capable. For individuals whose native with most enables them to overcome momentary lapses or to effectively pre-plan against failure, are those least armored in humility and least-likely to insist on the detail-by-detail, action-by-action, step-by-step checking that alone can spot and as necessary correct, or after its eventuation, account, for any unplanned, inadvertent, mishap. This fundamental problem is aptly and readily summarized in the phrase: "There's many a slip twixt the cup and the lip."

What if a patient finds that the pill dispensed is not what it should be (it is broken, contaminated, or just the wrong dose or medication)? What if a patient (user) takes out a pill too many? Or experiences a momentary interrupt and wants and/or needs to first put the pill back (for safekeeping), so she must be reminded again shortly to take that dose? Suppose the patient is feeling too poorly to take a dose and elects to skip doing so? Or decides she can tolerate only a partial dose? What if a patient has dropped the dispensed pill into the toilet or sink and cannot retrieve it, and so to take his dose, needs a second pill, now?

The prior art—especially as it presumptively links correct dispensation with the dose going into the patient—lacks feedback and error-handling tracking, resolution, and recording to account for divergences "between the cup and the lip"; it cannot adapt to the certainty of human imperfection, nor (for the most part) handle what must happen when the presumption embedded in the prescription fails to match reality.

Admittedly no device or system can be perfect; for while humans can devise myriads of ways to ensure that a dose is actually taken, a resisting patient can respond with a like count of ways to subvert such efforts. Pills can be palmed, tucked under the tongue or into the cheek, or even swallowed and then vomited back up. These measures can defeat even the 'gold standard'—as experienced medical personnel in psychiatric wards and perhaps a majority of cat owners can attest. The present invention presumes at minimum some level of acceptance (even if grudging or confused) as to the necessity and desirability of adhering to a prescription regimen, rather than active and intentional efforts to subvert and defeat it.

All of the above inventions, because they presume perfection can be engineered into a device used by imperfect people, lack feedback that measures when the theoretical regimen and reality fail to match, means to identify the incident(s) of divergence, error-recording means to track divergences, fallback means to recover from a presumption's failure, or any set of the above; and for each point of presumptive perfection lack in-process, situational, corrective capabilities to handle a divergence at the level closest in time and reality.

Additionally, existing systems that do not track errors by definition fail to maintain an accurate audit trail for post-administration review by medical personnel, and thus cannot confirm proper medication administration whenever an error is experienced. Existing systems are further generally impractical in that they fail to address many aspects of feedback (and non-adherence) which may be critical to proper evaluation of the prescription regimen as it has been experienced by the user, rather than as it was intended and prescribed originally by a medical service provider.

The need for the present invention becomes clearer when the perspective of 'need' shifts from that of the provider of the medication to not the provider of the dispensing device, but the user thereof, i.e. the patient.

To solve the problem of errors and divergences at the precise moment of delivery, slips must be looked for and corrected or else recorded exactly and as they occur—thereby providing immediate, specific, and bi-directional feedback as to the operation of the medical regimen in reality. The problem the present invention addresses, the question it asks is: What might be different between the plan (prescription) and reality (this medication this dose this time this user)—and how can the user match the 'should be' of the first to the 'is' of the second? In short, how differently would the prior art and the present invention handle the situation where a patient drops her dose onto the floor (or worse, into the toilet)?

SUMMARY OF THE INVENTION

While other systems have been proposed to ensure such proper usage of medication, it is only the present invention that addresses the real problem and provides the necessary tool for the best approach—at least one short of direct, experienced and professional human supervision—to the medication management problem. Because the present system integrates a reality-based testing of what actually is provided, when, under what constraints, and for whom, against the theoretical dictates of the prescribed and medically-approved plan, and accounts for divergence(s). All three points of the specific medication (the right choice, count, and dosage) are checked; as are all three points of the prescription's regimen (for this specific patient, at this specific time, and with an acceptable condition actually being experienced by the patient when the dosage is taken). The device comprises sensory testing for both inputs and outputs to effect responsive feedback loops which match either match the actual behavior to the prescribed regimen, and or validated and account for (record) errors and changes at the moment, and points, of dosage. So while there may come many a slip twixt cup and lip, if for each little slip there's an immediate record and fix, then nary a harm comes from such promptly fixed blips.

DETAILED DESCRIPTION

Figure 1:
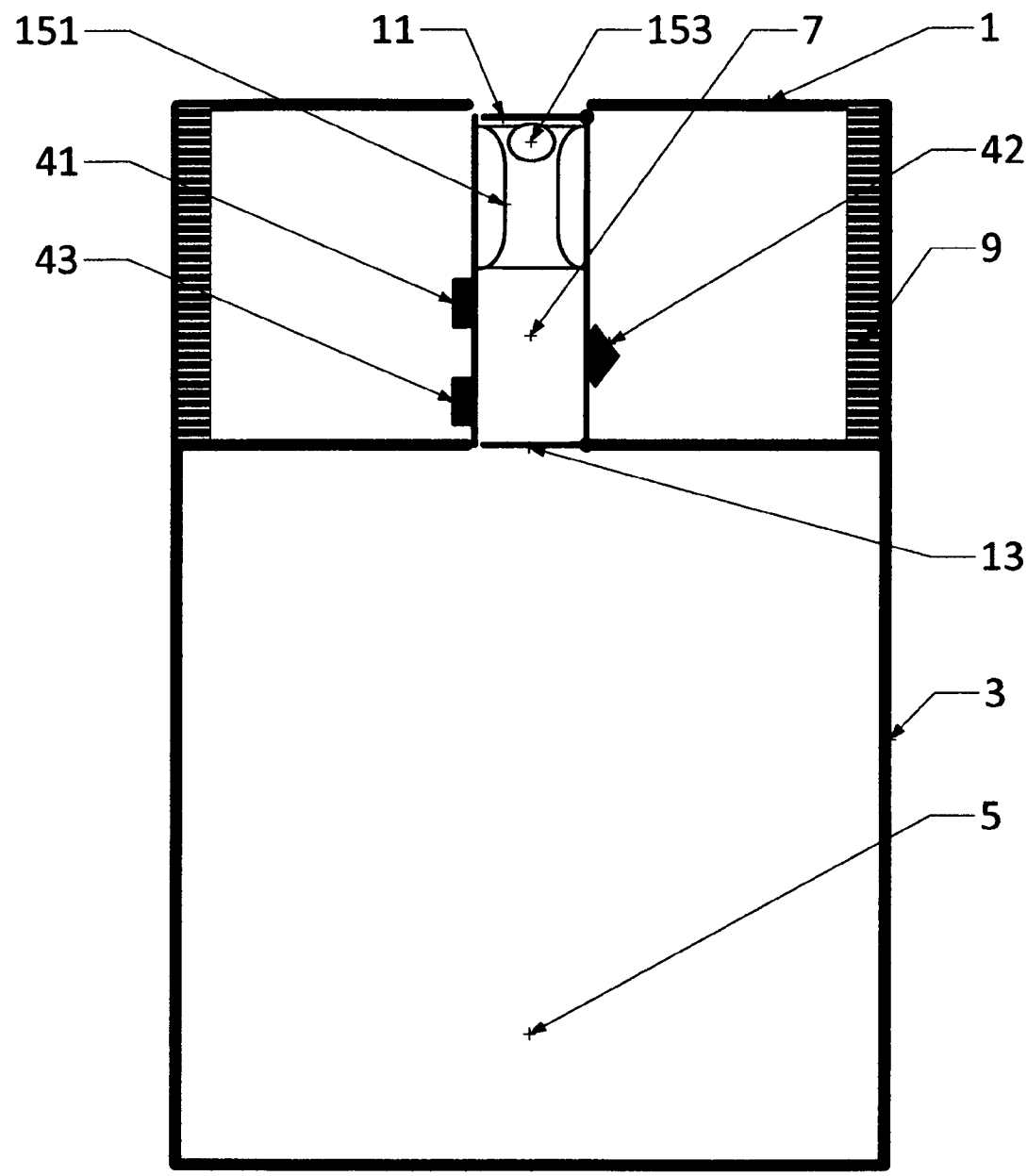
FIG. 1 is a side, cut-through view of a first and simpler embodiment of the invention showing an Operations Cap [1] having standard attachment means [9] by which it is removably but fixably attached to a container [3], that closes off an opening of the container [3] to constrain that connection between the outside world and an interior Storage Volume [5] of the container [3] through a distal Filling Door [11] into a Dose Checking Tunnel [7], and then through a medial Filling Door [13] into the interior Storage Volume [5], by and through which the Operations Cap [1] governs passage of medication into and out of the container [3] and thus controls the filling and dispensing of any dose and unit of medication to or from said storage volume according to said pre-set regimen.

"It isn't what we don't know that gives us trouble; it's what we know that ain't so."

Will Rogers

Medicine is practiced, not perfected; doctors treat from probabilities more often than certainties. In medication regimens the greatest preventable harm arises not from an intention, but a mistake which creates a divergence between what is planned, and what really happens. A prescription describes a plan to provide the patient with a series of events, each of which is the dispensation of a specific dose of a specific medication in accord with constraints of acceptable time and conditions, followed by the taking of that medication by that patient within those constraints. Reality is what happens; and in reality any or all of the dose, identity of medication, identity of patient, and time and condition constraints, may diverge from the plan.

Instead of presuming the simplest case (perfect adherence of performance to plan), the present invention presumes that errors can occur, should be detected, should be corrected as feasible, and most of all, that divergences should be tracked and reported to best effect the overall assessment of the quality of the experienced (as opposed to planned) treatment.

DEFINITIONS

The term "container" can include not only a receptacle for a medication, but also an appliance for storing and decanting one or more individual doses of a medication. One non-exclusive example of such a container—an appliance for storing and decanting a medication—is a vaporizer that provides medicine for a patient to inhale; another is a pre-filled syringe that provides a medicine for a patient to inject him/herself with.

The word "exemplary" is used herein to mean "serving as an example, instance, or illustration." Any aspect described in this document as "exemplary" is not necessarily to be construed as preferred or advantageous over other aspects.

The term "image-identify" and/or "image identifications" means to use images that may be obtained and transmitted across a wireless communications system to identify a patient at least by facial recognition, optionally a medication provider at least by facial recognition, a medication, a label for a medication disclosing at least the medicine and other useful or required information, and/or a container for the medication. These terms therefore include the capability of an instrument to capture, store and transmit biometric features of a person, including, but not limited to, fingerprint, footprint, and iris data, for identification and/or authentication.

The term "instrument" in combination with the words "mobile wireless communications," means and includes at least any of: a cellular phone; a pager; a satellite telephone; a two-way pager; and any of a personal digital assistant ("PDA"), a portable data processor, a home entertainment system control box, a wireless local area networks and any other type of wireless device having wireless transceiving capabilities, which may include any personal communications services device ("PCS"), whether such wireless transceiving uses any of time division multiple access ("TDMA", a code division multiple access ("CDMA"), global system for mobile ("GSM"), universal mobile telecommunications system ("UMTS"), wideband code division multiple access ("W-CDMA"), evolution-data optimized ("EV-DO"), wireless local area network ("WLAN"), wireless personal area network ("WPAN") or other protocols and codes, for any of voice, visual, data, and text communication.

The term 'medicine' refers to a substance or compound accessible to the user either as a non-prescription (over-the-counter) or prescription (only available through a licensed dispenser) purchase; and it may be any of a vitamin, a nutritional supplement, a mineral or chemical substance or compound (plus any stabilizing, transportative, or ameliorative additional substances such as the filler, solution, patch, or binder). In a slightly less-formal phrase, this is also a 'drug' (without the connotative freight of suggested or implied illegality of use, as might be confusing when referencing 'medical marijuana' whose legality depends on both geographic and political positioning).

The phrase "Mobile wireless communication instrument" means a device that is able to transceive electromagnetic signals without cables, with any of a wireless communications system (comprising an array of operatively-connected communication devices which may also include a wired telecommunications portion), satellites, (including satellites that are part of the Global Positioning System (GPS), Galileo, GLONASS, NAVSTAR, GNSS), a system that uses satellites from a combination of these systems, or any Satellite Positioning System (SPS) subsequently developed). As used in this document, an SPS also includes pseudolite (pseudo-satellite) systems.

The term "patient" means any person who is under medical care or treatment who requires use, ingestion, and/or injection of a medication.

The term "prescriber" means any person authorized to prescribe and/or dispense a medicine, as well as any person authorized to confirm compliance by a patient in a treatment plan using such medicine.

The term "provider" means any person authorized to physically provide and/or dispense a medicine, as well as any person authorized to confirm the fact of prescription for or dispensation to a patient of such medication, as part of a treatment plan using such medicine.

The term "static memory" means non-transitory computer-readable media (both Read-Only and Read-Write memory) that does not depend on continued electrical power to retain its stored values, as contrasted to "dynamic memory" which, while it also can be Read-Write memory, will lose its contents when power is not provided.

The term "validation protocol" means a procedure for comparing and collating any of codes, images and related data (e.g. voice- or finger-print) that enables an individual, whether patient or medical prescription issuer ('prescriber') or medical prescription provider ('provider'), to identify and authenticate transmitted information as being sourced by another individual with whom such communication and permission to treat are currently authorized, particularly when such communication concerns any of the specifics of a choice of medication, correct dosage, and correct timing for ingestion or use of a medication. The validation protocol may include a combination of at least a visual image of the patient, a visual image of the container or vial in which medicine is dispenses to the patient, a visual image of a label disclosing the associated medicine and other useful or required information about the medicine, optionally a visual image of at least one sample of the medication, and/or optionally a visual image of a medication prescriber or provider, or a textual representation thereof. The validation protocol may be included in a computer processor and/or data processor that present visual images and other parameters in the validation protocol, and may also present step-by-step requirements as to conditions external to or internal to the patient which the prescriber and/or provider requires to serve as predicates to using and/or ingesting a medicine.

Overview

The invention starts with: a user (hereafter generally referred to as a 'patient' i.e. a person seeking to treat an illness); a prescriber and/or provider who as part of a plan for treatment for the patient, authorize the possession and use, of at least one legally-possessed substance (which generally is a 'medicine' or 'drug') of which a determined amount (dose) is to be assimilated (it may be eaten, inhaled, injected, applied to or through the skin, or inserted through a natural or artificial orifice) into the patient's body for its beneficial effect; said authorization and use following a treatment plan, which is a schedule of actions for the patient to take (i.e. assimilate) a series of doses over time; a treatment regimen, which is the series of actual experiences of the patient in following the treatment plan; and a goal of effecting and recording the treatment regimen which recording correctly tracks the actuality experienced by the patient and will, can, and should be used in any review by any of the prescriber and provider when considering continued use or treatment of the patient.

Whenever there is an error (whether of omission or commission) in, or a deviation (by chance or choice) from the treatment plan, the specifics thereof are noted and recorded and incorporated into the treatment regimen. In addition not only are errors or omissions which can be and are corrected within the acceptable bounds or window therefor, also recorded (along with the correction), but also post-issuance changes to the treatment plan are authorized, validated, effected, or even disapproved and forbidden, and as such then incorporated into and recorded in the (now-altered) treatment regimen. It is the reality, not the plan; the regimen, not the prescription, that should govern evaluation and continuing care of the patient and his or her use (or not) of each medicine.

Typically a medicine comes in a given concentration and volume and/or weight (20 grams, 3 milliliters) for each single 'unit'; and a dose will comprise a number of such units (1 or more, or a readily-divisible fraction e.g. '½ pill', '¼ dose'). For example, a common statin is sold in units of 1 pill incorporating 600 mg of gemfibrozil, with a standard dose being a single pill; a standard anti-anaphylactic-shock effector comes in a unit as a single-use autoinjector delivering 300 µg of epinephrine at 1:1000 concentration, with a dose being that one usage; and a common B2-adrenergic receptor agonist comes in a pressure-releasing inhaler delivering 108 mcg of albuterol sulfate in microcrystalline suspension per inhaler activation (or 'puff'), with a dose being two activations. The late-night comedian line "take two aspirin and call me in the morning" has the unit of 'one pill' and the dose at 'two units'. (We cannot tell whether a dose is 2*81 mg 'baby aspirin'=162 mg, or 2*325 mg 'standard adult aspirin'=650 mg; but we can be sure that 325 mg is equivalent to the '5-grain' English apothecaries' measure.)

For ease in following the description of the invention, the embodiment that is generally described hereafter will be that handling those drugs embodied as a set of pills (whether in solid, gelcap, aerofoam, or other self-contained ingestible or insertable form). Other physical forms (e.g. vials, injectors, patches, even liquids and powders) which can be placed into the container, removed from the container, and replaced back into the container without transforming or deteriorating the drug, can be managed with means that are known to the prior art; however, those medications which are affected by the distribution such that they cannot safely be replaced unchanged, are not within the scope of the present invention.

The treatment plan will specify the dose, timing intervals, and external and internal conditions (or constraints) that should govern the user's taking (assimilation) of the medicine. The treatment plan is what the prescriber prescribes— but what happens thereafter, is what the patient experiences. Temporal causality ensures that a treatment plan can neither prevent nor record any deviation(s) or the causes and purposes thereof the user experiences after the plan is made.

The present invention focuses on not the perfection of adherence to the treatment plan, but the feedback and experience which constitutes the regimen. It presumes there will be slips—and thus there must be both adjustments to, and tracking of, such changes. It does these, rather than seeking the impossibility of plan-perfect treatment.

The treatment regimen is the actual experience, i.e. the series of doses as actually taken. It, not the treatment plan, is what medical supervision and decision-making should be based on. However, in all post-hoc determinations and assessments the treatment regimen will be presumed to be identical to the treatment plan in the absence of any record of deviation(s). The more the treatment plan and treatment regimen differ, the less effective (and possibly more harmful) the medication is likely to be. Even the very best and most powerful medication is of no use if never taken, or if it is only taken in direct contravention to constraints which deter it from being effective. All of overdoses, underdoses, adverse reactions, and ready tolerance despite contra-indicating conditions, should be recorded in and considered during the review of the actual treatment regimen.

A dose will be the number (whole, fraction, or combination thereof) of pills necessary to establish the effective concentration of the drug in the patient's body. Thus, the unit count for the dose is one aspect of both treatment plan and regimen. Each dose must be tracked as to its unit count, for having less or more than the planned number, certainly may effect both the timing of the next dose, and the effectiveness of the treatment regimen as experienced by the user. Adjustments may be required and if effected, recorded as part of the feedback process during the treatment regimen.

Timing intervals may have fixed or floating durations, and durations may have minimum and maximum ranges. (This enables a functional concentration, but not a harmful concentration, to be maintained in the user's body). The prescriber or provider may also set a 'dosing window', i.e. a level of acceptable imprecision in the timing (e.g. "plus or minus ten minutes") to allow for human imperfection in temporal exactitude. As long as a dose is taken within the dosing window, the timing interval to the next dose need not be reset.

External conditions specify what must (or must not) be true for the assimilation to effect the desired concentration in the body. Exemplary external conditions include whether the patient has eaten something no more than 20 minutes before assimilating the dose, or has not eaten anything for at least 2 hours before assimilating the dose (depending on whether the intake of food cushions, blocks, or may interfere with the assimilation); or whether the patient has slept, or had a bowel movement since the last dose, or the temperature at which the medicine was stored exceeded high or low limits for guaranteed stability, etcetera. Internal conditions specify the presence or absence of symptoms (nausea, disorientation, excessive fatigue or muscle soreness) or testable values (temperature, blood pressure, heart rate) indicative of the safety or potential for harm from assimilation. Exemplary internal conditions include 'do not take if nauseous'; 'do not take if dizzy or disoriented', 'do not drive after taking', 'do not use inhaler if unable to breathe normally', or 'do not take if blood pressure exceeds either 150 systolic or 85 diastolic').

The patient is given a medication in a container which holds at least one, and generally a plurality of doses (enough to last under the treatment plan until the next planned review by the prescriber). Generalized instructions and explanations are usually also provided; but these are now usually both extensively filled with boundary constraints and warnings, and for a prophylactic purpose more aimed at preventing providers' liability than use-specific instruction. Either the prescriber or provider may give the patient specific instruction as to such dosage, timing, and constraints particular to that patient for that treatment plan for that medication; and then the patient departs from the provider's direct observation and control until the next review.

A further complication is that certain doses may be optional—for that specific dose at that specific time—within a treatment plan. A treatment plan may allow as few as one, or as many as twelve, doses in any 24-hour period; or allow 3 doses in 24 hours but require both a minimum gap of four hours and a maximum gap of 12 hours between doses. The specifics of timing and constraints must be evaluated each time the user either seeks, or should seek, to take a dose.

DETAILED DESCRIPTION OF THE DRAWINGS

FIG. 1, the drawing of a first and simpler embodiment of the invention, also shows the distal Filling Door [11] and medial Filling Door [13] at each end of the Dose Checking tunnel [7]. Each Filling Door [11, 13] in the preferred embodiment is both latchably controlled by the Operations Cap [1] and also embodies a sensor known to the art that detects whether that Filling Door [11, 13] is opened or closed. These Filling Doors [11, 13] at each end of the Dose Checking Tunnel [7] enable a controlled, unit-at-a-time, check-and-count for anything being transferred into, or out of, the Storage Volume [5]. The scan-check-and-count sensors of the Dose Checking Tunnel [7] are further described below. FIG. 1 also shows how a Sizing Insert [151], specifically sized and shaped to the exterior dimensions of any two planes of a unit of the intended and particular medication (in this drawing, a pill [153], not claimed), can be fitted inside the Dose Checking Tunnel [7] to enable a rapid filling of the container [3] with suitable medication through a physical constraint enforcing volumetric, rather than purely visual, conformation with the desired shape and size. Each Sizing Insert [151] is additionally both so configured as to allow unobstructed sensing of each of the distal Counting Sensor [41], Identifying Sensor [42], and medial Counting Sensor [43], and also has an interior wall comprised of featureless, smooth, matte black colored, and low reflection material to least interfere with the Identifying Sensor [42] in its operation.

Figure 2:
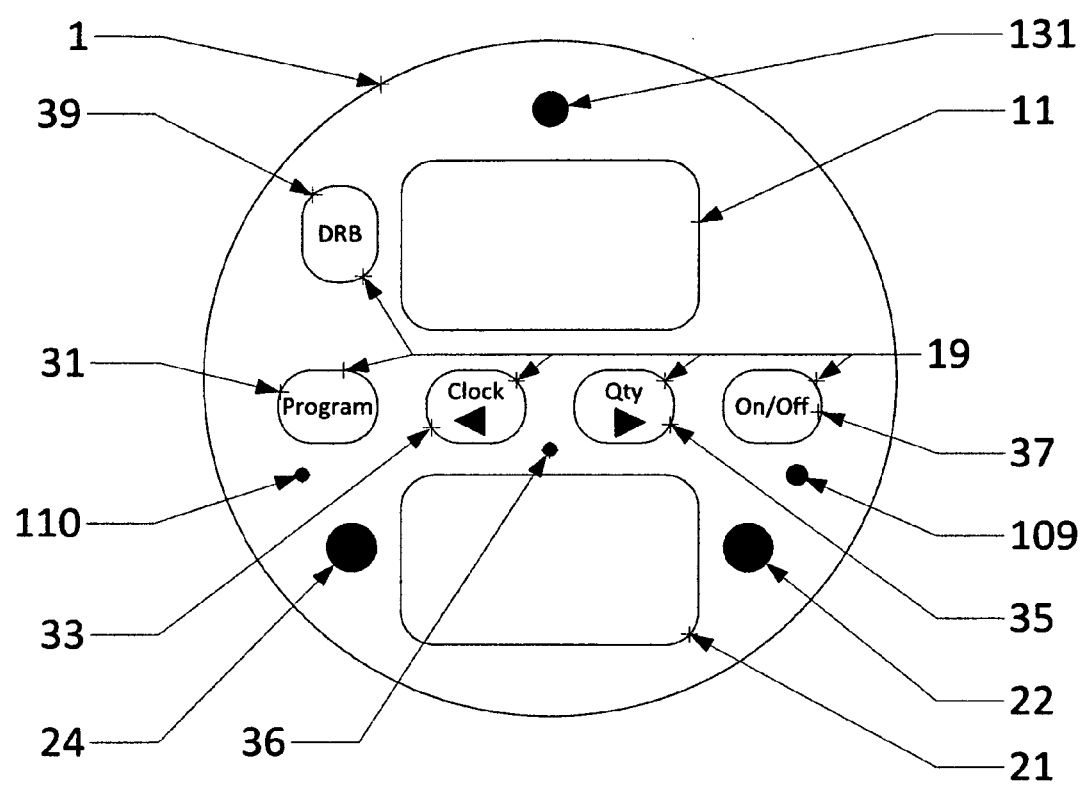
FIG. 2 shows the outside distal surface of the Operations Cap [1] as it would be seen by the intended user, who is a patient taking medication according to a prescription regimen provided by a medical provider (doctor, pharmacist, nurse, or other licensed and qualified medical person).

FIG. 2, the drawing of the outside surface of the Operations Cap [1] shows a Control Set [19], a Visual Display [21], and at least one red [22] and one green light [24] (for simple visual cueing) on the distal face of the Operations Cap. In the preferred embodiment, the Visual Display [21] is a liquid-crystal display; the lights [22, 24], LEDs.

The Control Set [19] is a set of buttons comprising operational, input, and programming controls for the invention. In the preferred embodiment these comprise a Program button [31], a Clock button [33] (which has a secondary function of a count decrementor), a Quantity button [35] (which has a secondary function of a count incrementor), an On/Off button [37], and a Dosing Release button [39]. Pressing the Dosing Release button [39] will start the process of delivering a dose from the Storage Volume [5] to outside the container [3]. In this initial embodiment the dose will be delivered to the patient through a bi-directional Dose-Checking Tunnel [7], and exit the container [3] at the Distal Filling door [11]; while in the preferred embodiment (shown in FIG. 14 and further described below), the dose will be delivered through a second, delivery Dose Checking Tunnel [159] (described below) to the Delivery Element [171] from where it will be retrieved by the patient; and a rejected dose will go elsewhere.

Also visible is the Reset button [36] which when activated provides the capability to reset the Operations Cap [1] to a predeterminable 'default' state (as it would come out of the OEM). This provides a means to recover from an electronic lockup or programming failure. All data, required or optional, in the database and/or memory which supposed to be entered by the patient, pharmacy, doctor, caretaker, etc. before starting use the device (any configurations), would be cleared from the static memory [51] and the dynamic memory [53]; the microprocessor, microcontroller or embedded controller [52] would be reset, deleting all I/O states; the Clock [55] would be reset to a "00:00" time, the Visual Display [21] would be blanked; and the power would be cycled. In the preferred embodiment activation of the Reset Button would take more than a single, short (<5 sec.) press to prevent inadvertent resets.

Figure 3:
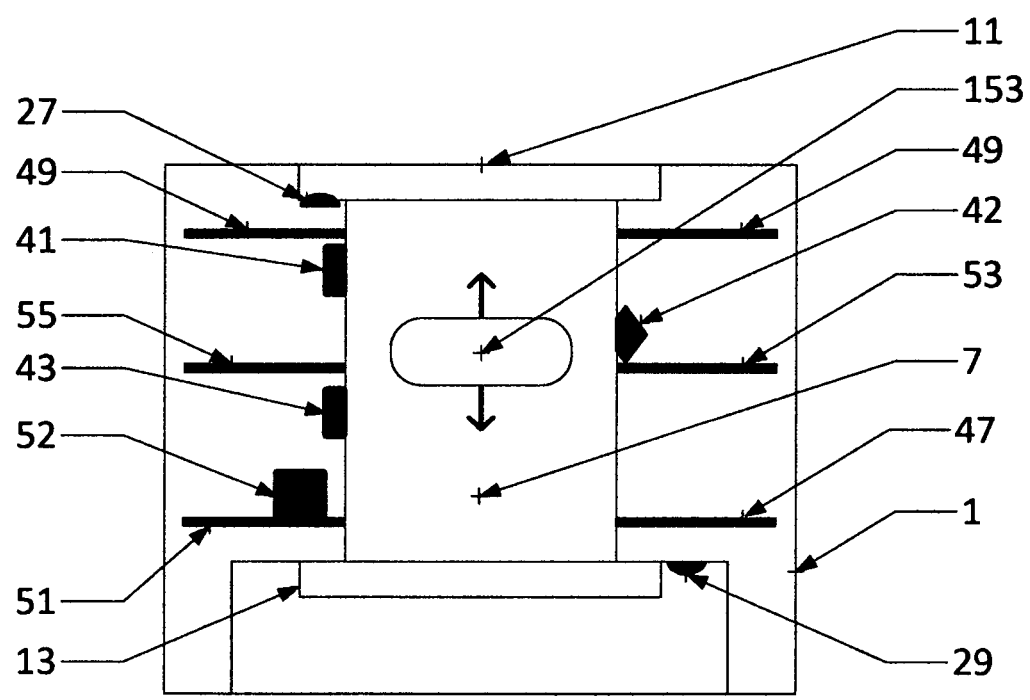
FIG. 3 is a cut-through view of the Operations Cap [1] showing details and internal elements of in and the Dose Checking Tunnel [7].

FIG. 3, a cut-through view of the Operations Cap [1] that shows details of it and of the Dose-Checking Tunnel [7], through which each unit of each dose of each medication is either fed into the container [3] (being passed through the bi-directional Dose-Checking Tunnel [7] from a distal-to-medial direction) and kept in the Storage Volume [5], or (being passed through the bi-directional Dose-Checking Tunnel [7] from a medial-to-distal direction) is delivered outward to the patient.

At the top is the distal Filling Door [11]; shown in this drawing is the embodied sensor [27] of any class known to the art that detects whether that Filling Door [11] is opened or closed. (The sensors for the other Filling Doors are not shown but are a part of the invention as described below.)

Below the distal Filling Door [11] at the interior surface of the Dose Checking Tunnel [7] is a Distal Counting Sensor [41], the distal of a linearly-separated (distal and medial) pair of sensors which enable the direction of movement of medication within the Dose-Checking Tunnel [7] to be correctly sensed; in the preferred embodiment this is a photocell, though it may also be a magnetic, frictional, physical, electric, optical, or other sensor as known in the prior art. Below the Distal Counting Sensor [41] is an Identifying Sensor [42] (described further elsewhere) used to identify the specific medication passing through the Dose-Checking Tunnel [7]. Below the Identifying Sensor [42] is the Medial Counting Sensor [43], the medial of the linearly-separated (distal and medial) pair of sensors, and at the medial end of the Dose Checking Tunnel [7] connecting it with the Storage Volume [5], is the medial Filling Door [13]. These paired Filling Doors [11, 41] and Counting Sensors [13, 43] at each end (distal, medial) of the Dose-Checking Tunnel [7], plus the intermediate Identifying Sensor [42], enable a controlled, unitary, scan-check-and-count of each unit of any medication to be stored into or dispensed from the Storage Volume [5] of the container [3].

Located within the Operations Cap [1] and around the Dose Checking Tunnel [7] are an Operations Set comprising at least one printed circuit board [49] on which the operative electronic elements are located, at least any of a microprocessor, microcontroller or embedded controller [52], both Static Memory [51] and dynamic memory [53], and an optional Clock [55]; all used to store and run operational program(s) and data, and all connected through any of a bus, baseplane, and backplane to the Control Set [19], and through the Operations Cap [1] to the battery.

Figure 4:
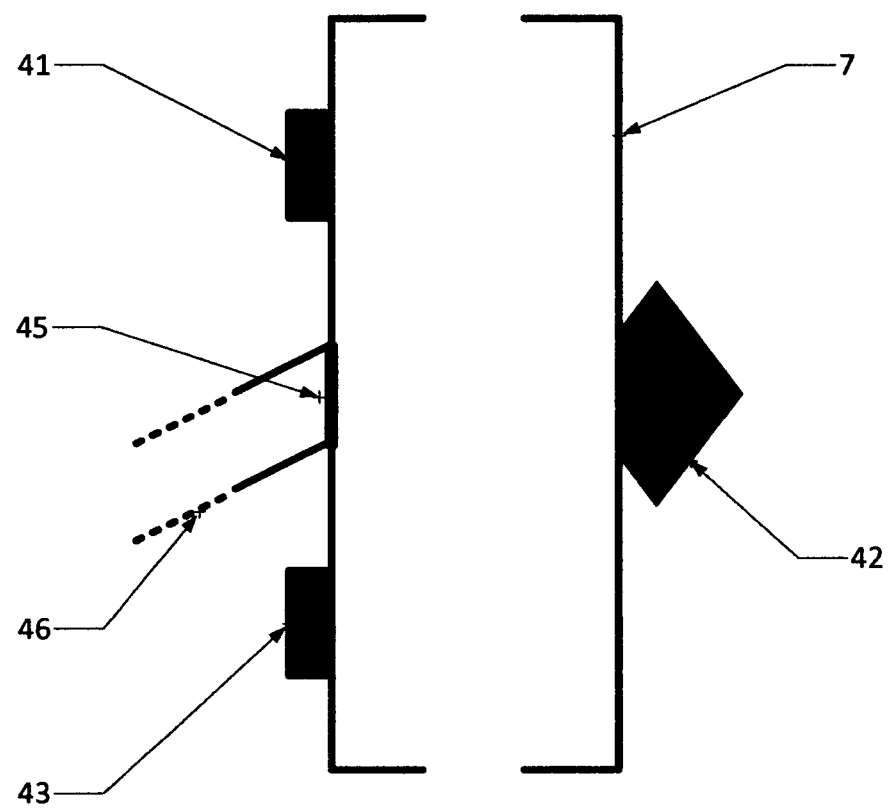
FIG. 4 shows a further and alternative embodiment of the Dose Checking Tunnel [7] which further comprises a Diversion Tube [46] connecting through a Diversion Door [45] controlled by the Operations Cap [1] through which unacceptable units (whether or not of the correct medication) are diverted into a separate Reject Storage [49].

FIG. 4 shows a further and alternative embodiment of the Dose Checking Tunnel [7] which further comprises a Diversion Tube [46] connecting through a Diversion Door [45] (as stated above, this embodies a latchable-door-and-sensor combination and is also controlled by the Operations Cap [1]) through which unacceptable units (whether or not of the correct medication) are diverted into a separate Reject Storage Volume [211]. The Diversion Door [45] and the Diversion Tube [46] are located both between the Distal Counting Sensor [41] and Medial Counting Sensor [43] and opposite the Identifying Sensor [42]. If a unit of medication (whether or not of the correct medication) when scanned by the Identifying Sensor [42] fails to match the pattern stored in the Operation Cap's Static Memory [51] then in this embodiment the Operations Cap [1] closes both the Medial and Distal Filling doors [13, 11], opens the Diversion Door [45], and thus diverts that unit as unacceptable through the Diversion Tube [46] into a separate Reject Storage [211].

Figure 5:
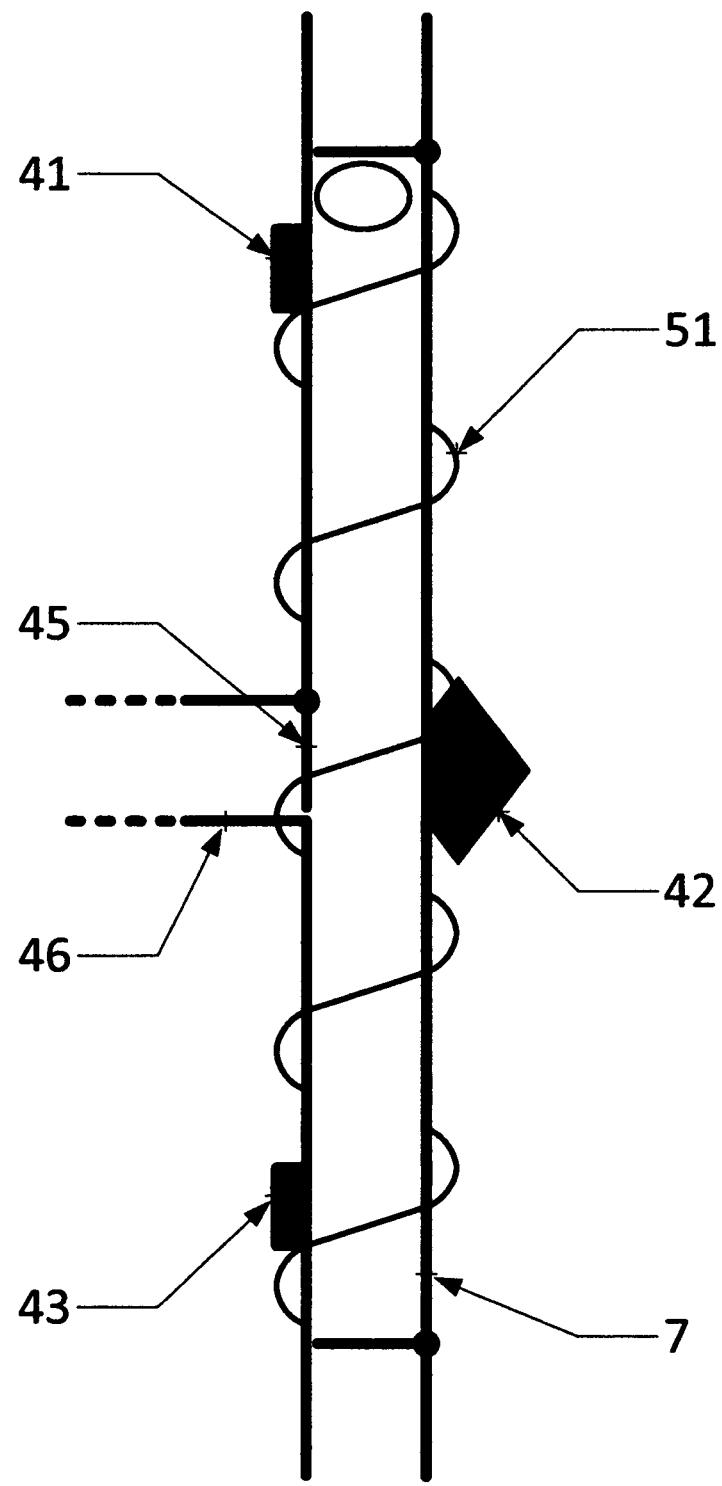
FIG. 5 shows a still further embodiment of the Dose Checking Tunnel [7] with a Transfer Means [51] (in this drawing an electromagnetically-driven coil) whose activation simultaneously transports the medication within the Dose Checking Tunnel [7] in a specific direction (in, or out, diverted; and as controlled by the Operations Cap [1]) and is recorded as effecting that specific direction of transfer.

FIG. 5 shows a still further embodiment of the Dose Checking Tunnel [7] further comprising a Transfer Means [51] (in this drawing an electromagnetically-driven coil) which is controlled by the Operations Cap [1]. Activation of this Transfer Means [51] both transports the medication within the Dose Checking Tunnel [7] in a specific direction (in 'medially', or out 'distally', or into the Diversion Tube [46]) and is recorded as effecting that specific direction of transfer. If the pill is to be discarded, as the pill reaches the Diversion Door [45] the Operations Cap [1] opens the Diversion Door [45] so either gravity, or a second pulse of the Transfer Means [51] at the far side of that Diversion Door [45], will move the pill into the Diversion Tube [46].

Figure 6:
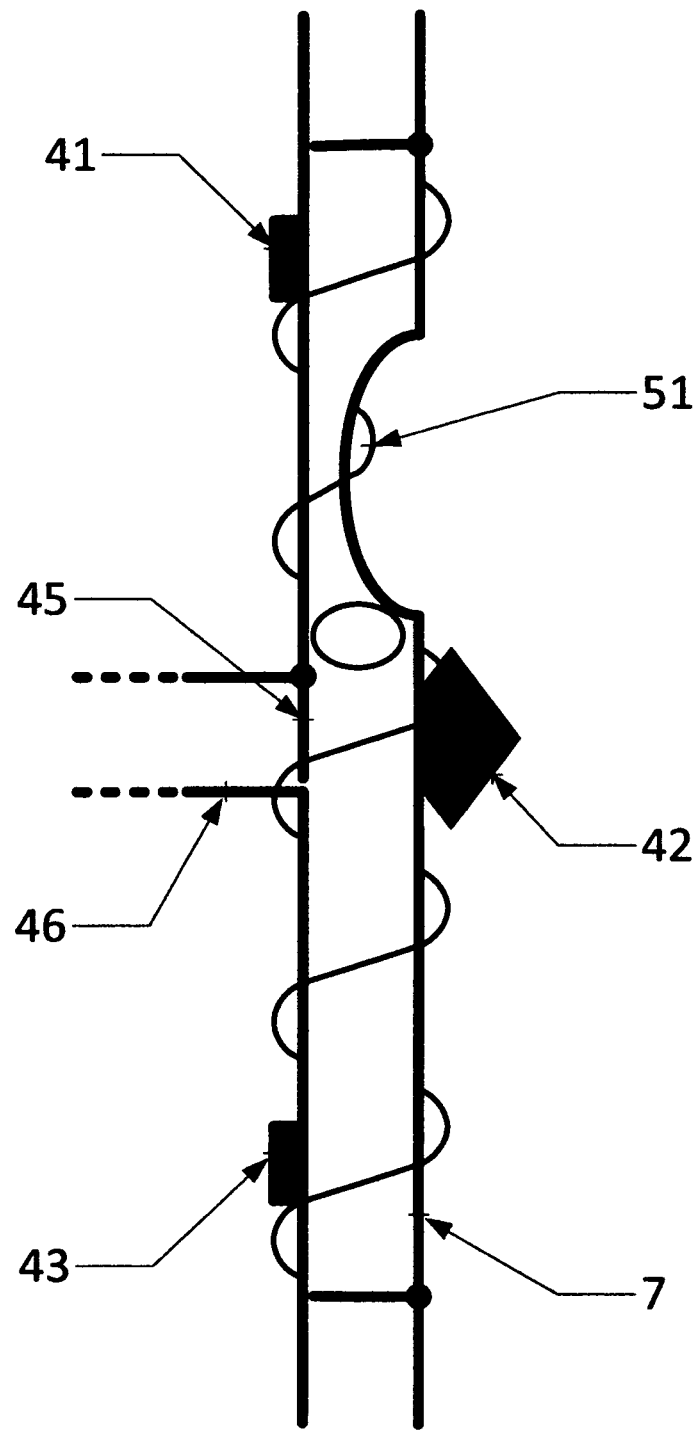
FIG. 6 shows that still further embodiment of the Dose Checking Tunnel [7] with the controllable Transfer Means [51] being activated to sequentially squeeze a pill within it so that pill is transferred from the medial towards the distal end.

FIG. 6 shows that still further embodiment of the Dose Checking Tunnel [7] with the controllable Transfer Means [51] being activated to sequentially squeeze a pill within it so that pill is transferred from the medial towards the distal end.

Figure 7:
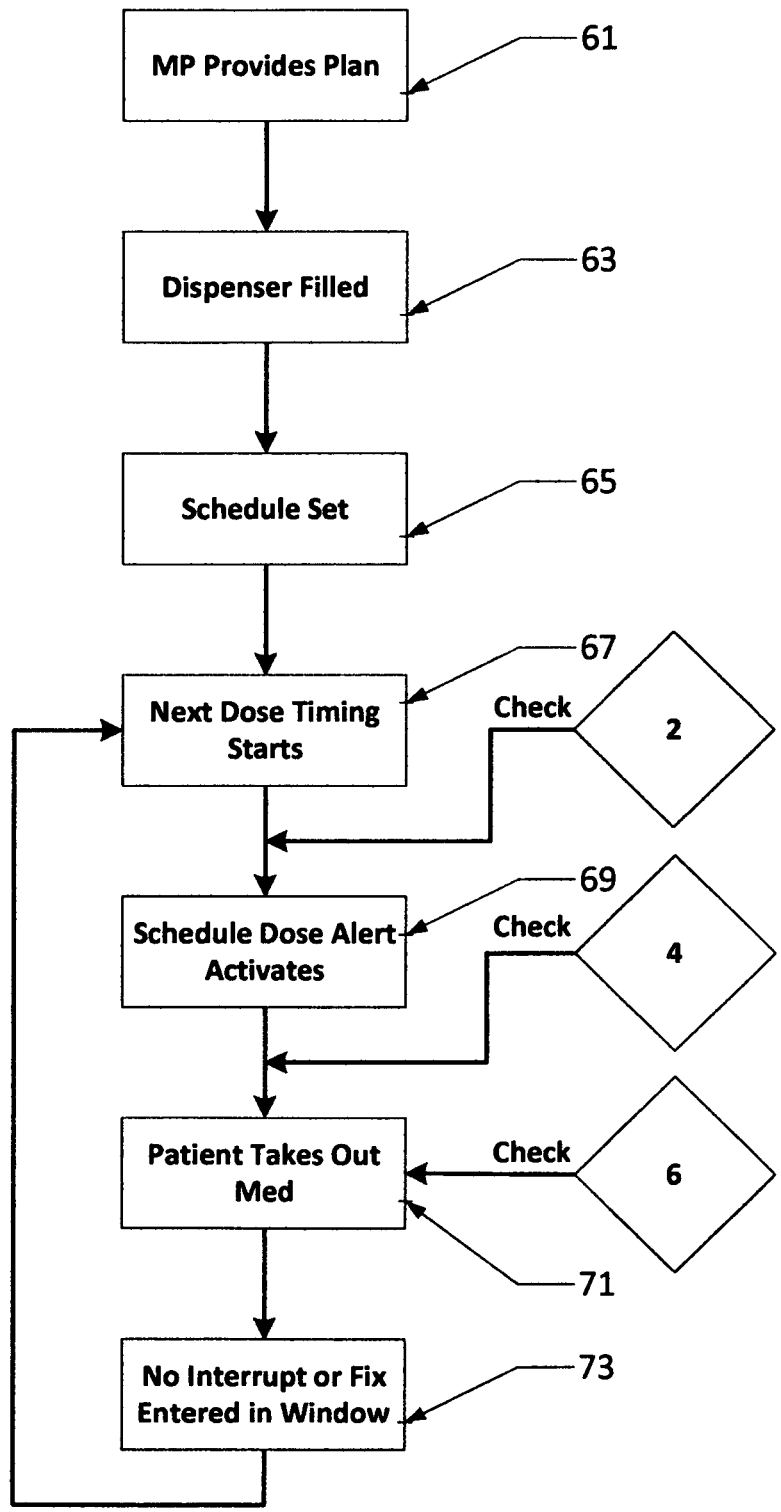
FIG. 7 is a flowchart of the overall operation, including the sensory feedback loops, tracking the operation of the device and its interaction with the user at the time each specific dose is scheduled, and thus intended, to be taken. (Feedback and correction/recording checkpoints 2, 4, and 6 are indicated but not detailed in this drawing.)

FIG. 7, the flowchart of the overall operation, starts when a medical prescriber provides both a treatment plan and a prescription (or, for non-prescription i.e. over-the-counter medications, an identifying description) for a drug, which the patient (user) is to use [61]. At this stage the treatment plan is sent to the Operations Cap [1] which will store the same in its Static Memory [51].

The user then will obtain the drug from a provider (for a prescription medication, a pharmacy and pharmacist) in the quantity deemed mutually acceptable (based on toxicity, control schedule, cost, risk or hazard of deterioration, etc.) to the prescriber, provider, insurer, and user; and the provider will fill [63] the container [3]. At this step, after each individual unit of the drug is placed into the distal Filling Door [11], it passes through the Dose Checking Tunnel [7] and if validated, the unit count will be incremented and the unit placed in the Storage Volume [5].

When the unit count equals the quantity set, the prescriber uses the Operations Cap [1] through the Control Set [19] to activate the medication schedule detailed in the treatment plan [65], and the time to the next dose (incorporating any agreed-upon Dosing Window) is calculated and the timer's count towards it begins [67]. The time (and in an expanded embodiment the specific details such as name of medication, unit count, ordinal dose count, unit description) for the next dose may be displayed on the Visual Display [21] continually or, to save power, only through using the Control Set [19].

Any exception to the dosing schedule requested between doses is handled according to the flowchart of the third feedback checkpoint [6] (see FIG. 10, also described below).

When the scheduled interval has elapsed the scheduled dose alert activates [69] and the first feedback checkpoint [2] (as to the correctness of medication, dose, and timing, described below in FIG. 8) is performed. Assuming the first feedback checkpoint [2] returns a correct result, if the alert has been given and the ready-to-remove dose is available, the second feedback checkpoint [4] (as to whether the patient removes, returns, or rejects the dose, or asks for a reset of the time, described below in FIG. 9), is performed [71].

Assuming the second feedback checkpoint [4] returns a correct result, and there is no interruption, request for exception, or request for a fix of an observed (by the user) error [73], then the schedule to the next dose is set (according to the time the dose is actually taken or rejected, and with attention to the compliance within or beyond the Dosing Window) and the operation loops back to the Next Dose Timing [67]. Any such request is handled through the third feedback checkpoint [6] at this state.

At any of the steps a validation feedback checkpoint ([8], in the form shown in FIG. 11) may be incorporated to ensure that only the individual(s) who is (or are) specifically authorized to effect that step, are personally aware of and in fact doing so.

Figure 8:
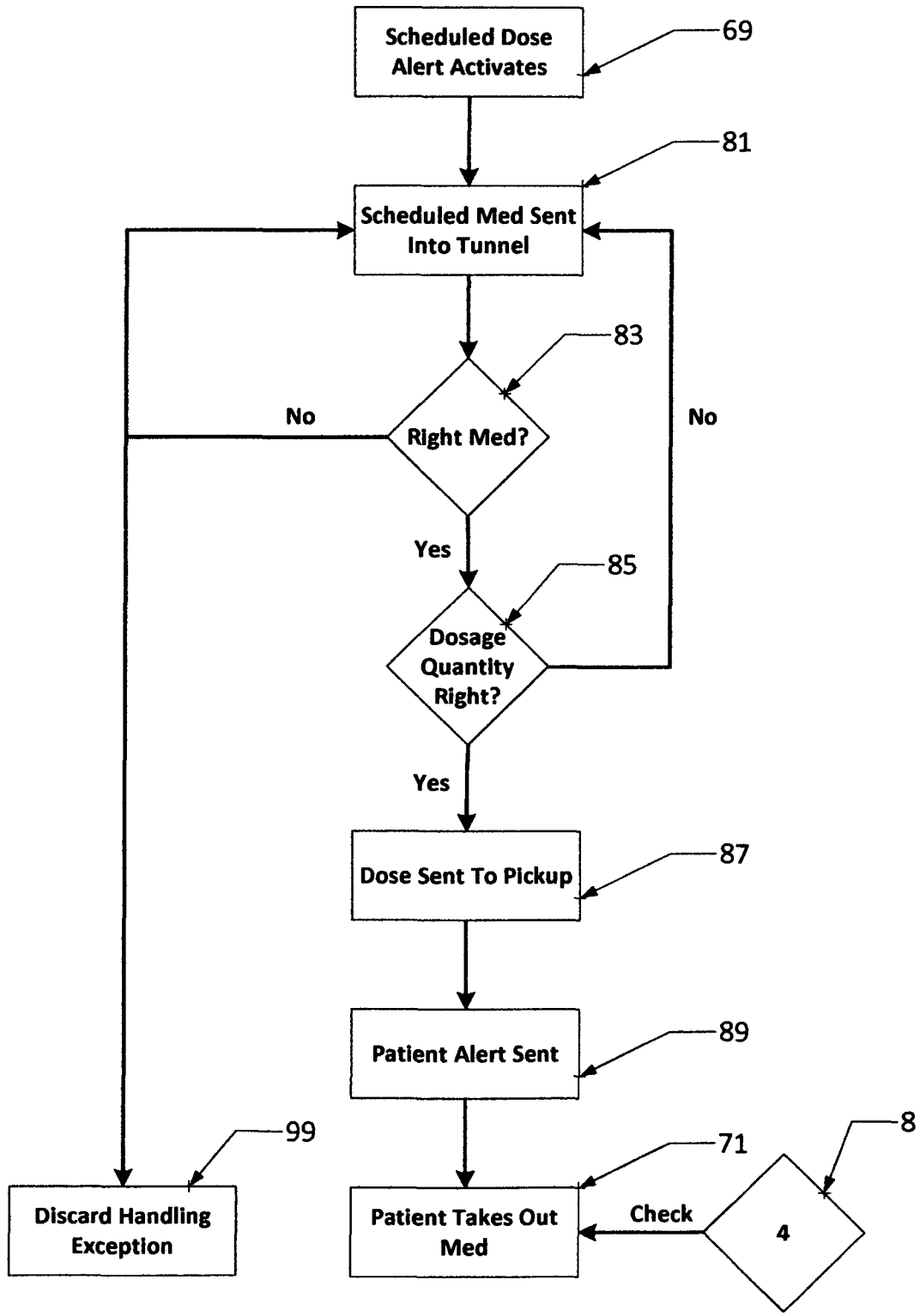
FIG. 8 is a flowchart of the first feedback checkpoint [2], that of testing and recording the prescription planned dosage, that is effected whenever a medication is actually made ready and the patient alerted to a scheduled dose, including a $4^{th}$ Feedback and correction/recording checkpoint for authorized dispensation of a dose to a recipient.

FIG. 8, the flowchart of the first feedback checkpoint [2] of testing and recording of a planned dosage, is effected whenever a medication is to be actually made ready and the patient alerted to a scheduled dose. When the scheduled dose alert activates [69], i.e. the timer reaches the time set for the next dose (within the accepted Dosing Window) and the patient seeks to obtain the dose (for example, by pressing the Dosing Release button [39]), the invention sends the scheduled dose [81] into the Dose-Checking Tunnel [7 or 159, depending on embodiment]. To effect this step, the medial Filling Door [13, 161] is opened and a first unit of the medication (and of that specific dose) is moved (by gravity or mechanical means known to the prior art, neither of which are claimed here) from the Storage Volume [5] into the Dose-Checking Tunnel [7, 159] at its medial end and the medial Filling Door [13] closes. That unit first passes in a medial-to-distal direction past the medial Counting Sensor [43, 175], which increments the unit count as the unit passes distally over it and records that passage; and then passes the Identifying Sensor [42, 172] which is used by the Operations Cap [1] to compare the observed feature(s) of that unit against the pattern(s) stored in the Static Memory [51] for the salient feature(s) of that class of unit, thus checking if this is the right medication [83].

If the pattern is not matched, the exception for handling an incorrect medication (one of possibly several 'Discard Handling Exceptions') is invoked [99], that unit is discarded, and the steps of sending [81] another unit from the Storage Volume [5] into the Dose-Checking Tunnel [7] and checking whether this is the right medication [83] are repeated. In a further embodiment of this invention, additional error handling processes are invoked after multiple failures to send out the correct medication.

If the pattern is matched then the unit count is incremented and compared against the dose count to check whether the dosage quantity is right [85]. While in many, perhaps even most cases, a single pill will comprise each single dose, if multiple pills are needed then the steps to send [81] and check [83] another unit are repeated, until the incremented unit count matches the dose count.

Once the incremented count matches the dose count, the pill(s) in the Dose Checking Tunnel [7, 159] are passed over the Distal Counting Sensor [41] and the Distal Filling Door [11, 173] is unlatched, so the dose (checked as to both identity of medication and count) is made available for pickup [87].

If the above steps have been performed independent of human effort (i.e. if the medical delivery, checking, and counting have all been autonomously performed) then at this point an optional patient alert is sent to the user [89], if he or she had not already received one, letting the patient (user) know that the dose is ready and available.

The dose having been made available to the user and the user alerted, the time continues to count through the period of any Dosing Window. A user may, at any time during a Dosing Window, pick up the device and, through activating the Control Set [19] (in the preferred embodiment, doing so by pressing the Dosing Release button [39]), seek to obtain the dose scheduled for that Dosing Window. An optional validation check [8] (see FIG. 11) can be run at that time. When the Dosing Release Button [39] is pressed the distal Filling Door [11, 173] is opened and the medication is removed by the user, the Operations Cap [1] records that dose and time as having been taken and sets the timer counting towards the next scheduled dose release, i.e. the operation loops back to the Next Dose Timing [67].

Figure 9:
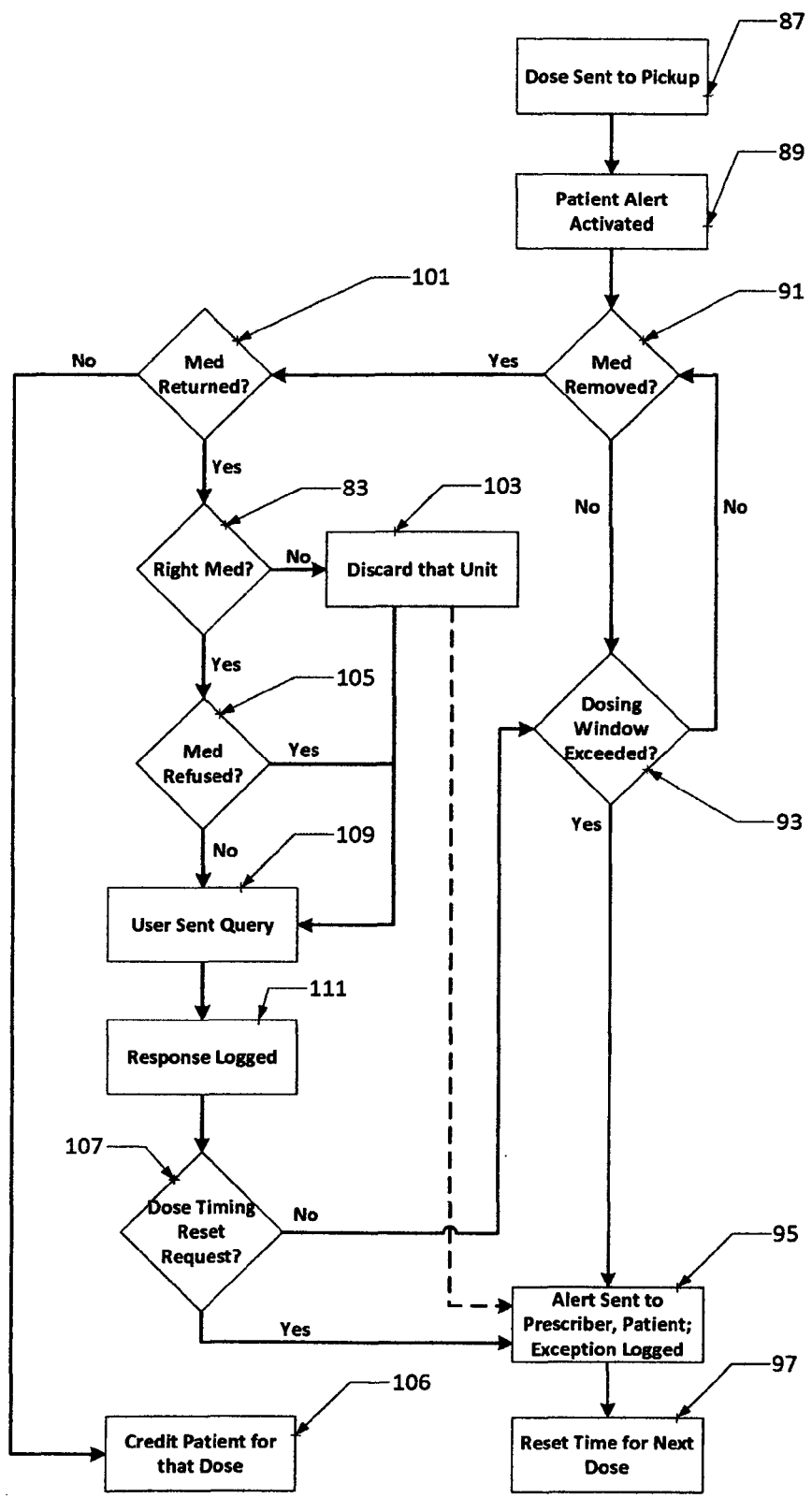
FIG. 9 is a flowchart of the second feedback checkpoint [4], that of testing and recording the taking of the prescription planned dosage or handling of an exception, as when a patient indicates that the dispensed medication was not and will not be taken.
Figure 14:
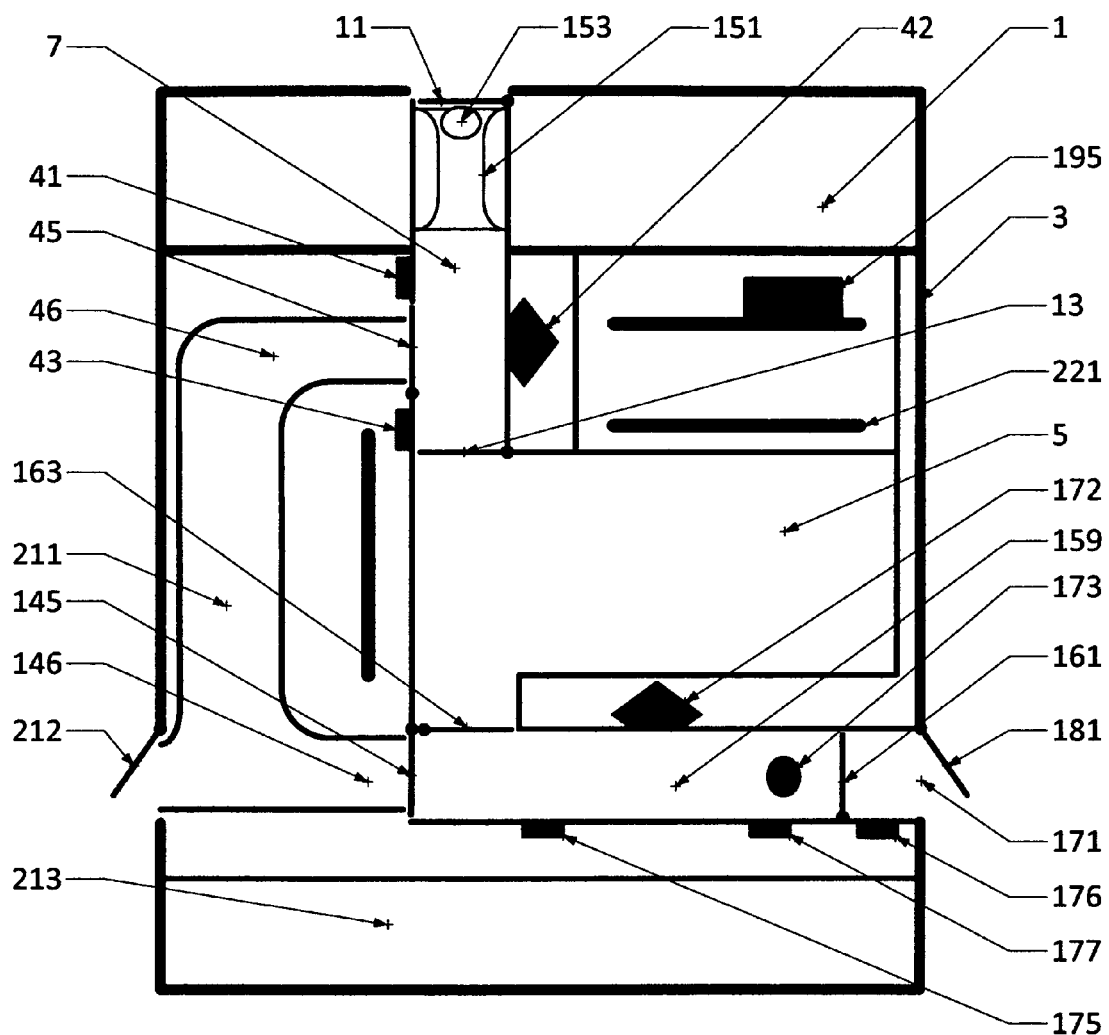
FIG. 14 is a drawing emphasizing the functional compartmentalization (i.e. the respective elements are not to scale) of an advanced embodiment of the invention wherein the container [3], with the Operations Cap [1] at one end, comprises both a Storage Volume [5] for the individual units of the medication which will be delivered to the patient as all (or the summed parts) of each dose, and a Reject Storage Volume [211] for individual units of the medication which either during filling, or during use, have been rejected. Also shown is a Delivery Element [171] and a Return Lever [173] by which the user can both receive a dose and return any unit thereof which, depending on whether it is acceptable or has been rejected, can be placed in the appropriate storage volume for re-use or discarding.

FIG. 9 is a flowchart of the second feedback checkpoint [4], that of testing and recording of whether or how a planned dosage is effected whenever a medication is made ready and the patient alerted to a scheduled dose, and includes handling of two common problems (i) the medication is not picked up, or (ii) is returned—and for the latter, two sub-problems of the medication being the wrong medication, or being refused. This expands the process summarized in FIGS. 7 and 8 as the step where, after a dose has been prepared (FIG. 7) for pickup [87] (and in the advanced embodiment of the invention as shown in FIG. 14, sent to the Delivery Element [171]) and a patient alert activated [89], the user is expected to, but does not necessarily, take out the medication [71].

For the duration of the Dosing Window the Operations Cap [1] waits for a signal that the dose has been removed from the container [3]. Depending on the embodiment, this can come from the activation of a latch sensor when the Delivery Gate [181] is opened, the opening of the distal Filling Door [11] after the Dosing Release Button [39] has been pressed once, or the indication of the MedPresent Sensor [176] that a dose is no longer present in the Delivery Element [171]. If the dose is not removed before the Dosing Window is exceeded [93], then to any set of the prescriber and patient a late dose alert is sent and an exception to the treatment plan is logged [95] into the Static Memory [51], and the Operations Cap [1] latches the distal delivery door (any of the distal Filling Door [11] and Delivery Gate [181], resets the time to the next dose [97], and sets the timer (in the preferred embodiment, its Clock [55]) counting towards the next scheduled dose release, i.e. the operation loops back to the Next Dose Timing [67].

If the medication is removed [91] and is not returned [101], then the user is credited with that dose [106] and it is logged into the Static Memory [51] as having been taken. If it is returned [101], then each unit is passed back into the container [3] through a Dose Checking Tunnel [7, 159]. As explained above each unit is counted and scanned and identified, i.e. during passage the Identifying Sensor [42, 172] compares that unit against the pattern(s) stored in the Static Memory [51] in the Operations Cap [1] the observed salient feature(s) of the unit, thus checking whether this is the right medication [83]. If a dose comprises more than one unit, the count of units returned is logged, but until the number not returned drops below an effective dose, the dose count is not reduced; and until the number count reaches the number of units delivered, the right medication has not been returned. If the count of unit(s) and dose returned matches those delivered, then no further action is taken and the returned unit(s) are restored to the Storage Volume [5] and the count of medication stored is incremented accordingly.

The user is queried via the Visual Display [21] whether he is refusing the unit(s) returned [105] and the response is logged [111] in Static Memory [51]. In a further embodiment the refusal response, and contextual data (time, count returned/refused/taken) is sent via the Remote Link [195] to the prescriber. (Not shown is the separate handling of an undercount, where the units returned are restored to the Storage Volume [5], the user is sent a query as to the location of any non-returned unit(s), and the provider is alerted as to the time and quantity of non-returned unit(s).)

If what is returned is not the right medication, then that unit is discarded [103], the user is asked why the wrong item was returned [109], and the user's response (or the lack thereof) and the failure of return are both logged [111], and the user is asked whether they request that the dose timing be reset [107], and (in a yet further embodiment, after a delay time to enable localized user correction, preferably within the Dosing Window) the logging and handling of the user's response is handled as described immediately above.

If the medication returned is the right medication and amount to leave a non-effective dose, or no dose whatever, then the user is asked whether the dose timing is requested to be reset [107]. If there is no such request then the user may yet take the dose out before the Dosing Window is exceeded [93]. If there is a request to reset the dose timing then the Operations Cap [1] logs the request and in one embodiment can send the request via the Remote Link [195] to the prescriber for approval and reprogramming, and in another embodiment reschedules the next dose according to the constraints of the treatment plan [97]. After this, whether or not the timing has been reset, the Operations Cap [1] sets the timer counting towards the next scheduled dose release, i.e. the operation loops back to the Next Dose Timing [67].

Figure 10:
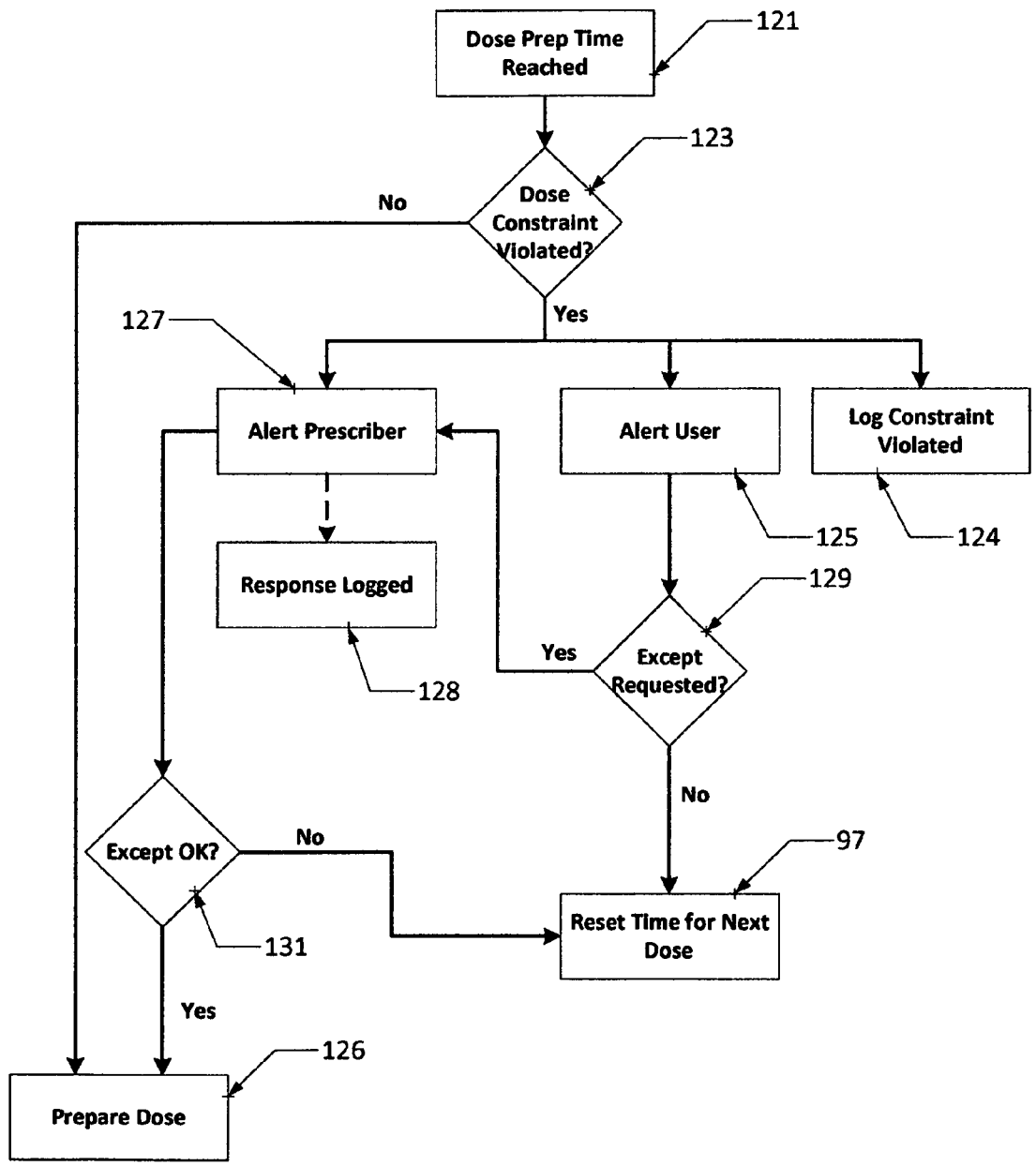
FIG. 10 is a flowchart of the third feedback checkpoint [6], that of testing and recording the taking of the prescription planned dosage or handling of an exception when a constraint (or limit) of the treatment plan is reached (e.g. the dose exceeds a maximum or fails to meet a minimum number of doses for a set time period, or for total doses; the taking of a critical underdose or critical overdose; a prescription renewal alert; a medication shelf-life limit; an external constraint; or a patient reporting a symptom of intolerance).

FIG. 10 is a flowchart of the third feedback checkpoint [6], that of testing and recording of a user taking the planned dosage according to the correct time and constraints, or in the alternative, handling of an exception when a constraint (or limit) of the treatment plan is reached (e.g. the dose exceeds a maximum or fails to meet a minimum number of doses for a set time period, or for total doses; the taking of a critical underdose or critical overdose; a prescription renewal alert; a medication shelf-life limit; an external, or environmental constraint; or a patient reporting a symptom of intolerance).

Each time that the Clock [55] matches up with a time within the limits of the Dosing Window as stored in the Static Memory [51] that is, according to the treatment plan, when it is time for a dose to be taken [121], the Operations Cap [1] uses all data to evaluate whether any specific constraint that would prohibit, or constrain, the taking of that specific dose has been violated [123]. If no constraint has been violated, then the dose is prepared for the user [126], and the operation loops back to the Schedule Dose Alert Activates [69].

If, however, a constraint has been violated (for example, too many doses within a 24 hour period) the Operations Cap [1] will (a) log the constraint and its violation [124], (b) issue an alert to the user [125], and (c) issue an alert to the prescriber [127].

If the user fails to respond or otherwise does not request an exception to the constraint [129], then the Operations Cap [1] will reset the time for the next dose [97] and set the timer counting towards the next scheduled dose release, i.e. the operation loops back to the Next Dose Timing [67].

If the user does request an exception [129] then this request is sent via the Remote Link [195] to the prescriber, whose response (or the lack thereof) is logged [128] and, if the exception is approved by the prescriber [131], the dose is prepared [126] and the operation loops back to the Schedule Dose Alert Activates [69]; while if the exception is not approved, it is not prepared; and then the Operations Cap [1] will reset the time for the next dose [97] and set the timer counting towards the next scheduled dose release, i.e. the operation loops back to the Next Dose Timing [67].

Figure 11:
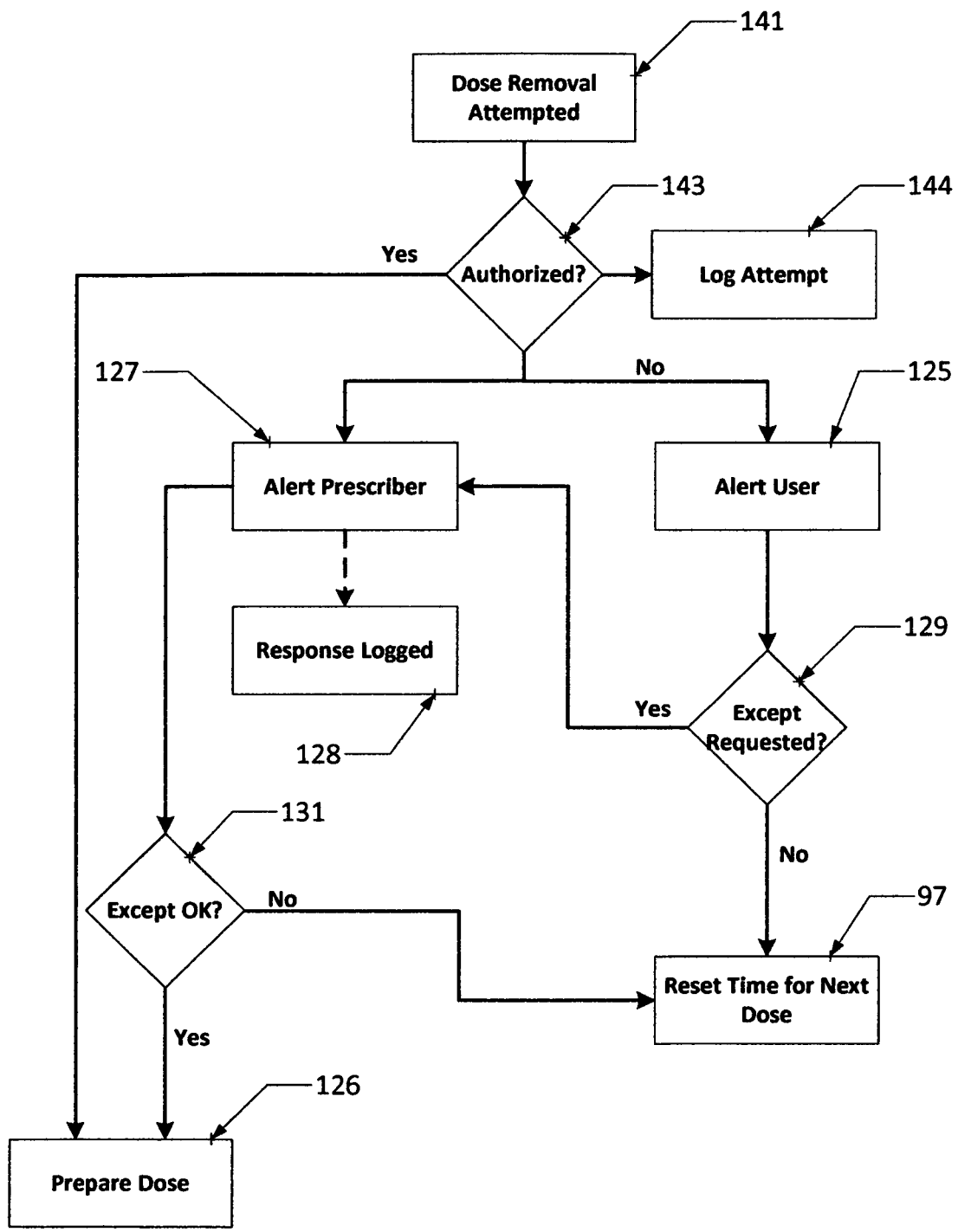
FIG. 11 is a flowchart of the handling of a fourth feedback checkpoint [8], that of testing and recording the validation of a user's interaction with the invention through an authorizing process (which may incorporate additional hardware, firmware, and software; and use any of a number of alternatives known in the prior art and not separately claimed).

FIG. 11 is a flowchart of the fourth feedback checkpoint [8], that of testing and recording the validation of a user's interaction with the invention through an authorizing process (which may incorporate additional hardware, firmware, and software; and use any of a number of alternatives known in the prior art and not separately claimed). While authorization may be required to fill (or re-fill) the container [3], to program the Operations Cap [1], to empty out the Reject Storage Volume [211], to authorize an exception to a constraint [131] (as in the preceding paragraph), the most typical authorization checkpoint may be when a user attempts to remove medication from the container [3] via the Delivery Element [171] or, for the first and simple embodiment, from the distal Filling Door [11].

In any embodiment where any authorization is required, then any of the latchable door-plus-sensor elements that would allow the removal of anything from the container [3] default to a locked state when there is any medication that door-plus-sensor gives access to. Upon a dose removal attempt [141], the Visual Display [21] will prompt the user to enter, using the Control Set [19], the validating authorization, as described further below. Upon receiving the response the Operations Cap [1] determines, through matching the provided input against the required pattern stored in the Static Memory [51], whether or not this specific taking of the medication is authorized [143] and logs the attempt plus contextual information (time of day, location of container [3]) [144]. If the user is authorized (i.e. if the patterns match) then the Operations Cap [1] will release the specified latch and thus release the dose [126] and the operation loops back to the Schedule Dose Alert Activates [69]. (In a further embodiment, not shown, the Remote Link [195] can be used to report the attempted access to the prescriber, or to let the prescriber authorize the access.)

If the user is not authorized, then the user is alerted to his (or her) invalidity [147], and an alert reporting the attempt is sent to the prescriber [127]. The lack of authorization thus is treated as an external constraint. If the user fails to respond or otherwise does not request an exception to the constraint [129], then the Operations Cap [1] will reset the time for the next scheduled dose release [97] (if the time has elapsed) or keep the timer counting towards the next scheduled dose release (if the time has not elapsed) i.e. the operation loops back to the Next Dose Timing [67].

If the user does request an exception then this request is sent through the Remote Link [195] to the prescriber [127], whose response (or the lack thereof) is logged [128] and, if the exception is approved [131], the dose is prepared [126] and the operation loops back to the Schedule Dose Alert Activates [69], while if the exception is not approved, then the Operations Cap [1] will reset the time for the next dose [97] and set the timer counting towards the next scheduled dose release, i.e. the operation loops back to the Next Dose Timing [67].

Figure 12:
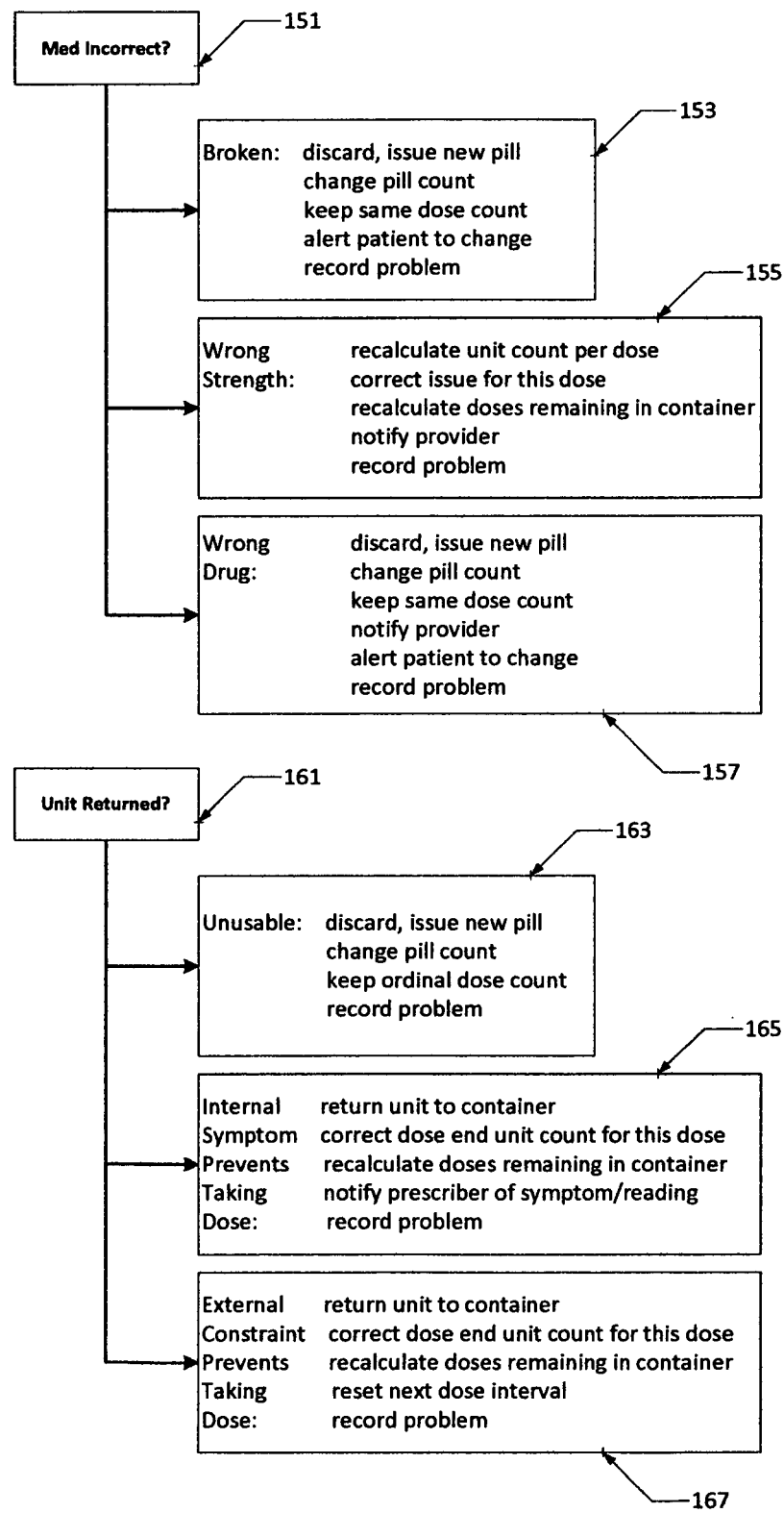
FIG. 12 shows in summary form a hierarchy of 'stacked' contingency plans (with specified sub-processes) for handling and recording a set of common exceptions which may be experienced during the treatment regimen.

FIG. 12 shows in summary form a hierarchy of 'stacked' contingency plans for handling the most common exceptions which may be experienced during the treatment regimen. One class of mistakes is comprised of the situations when the Identifying Sensor [42] fails to match the unit in the Dose Checking Tunnel [7, 159] to the pattern for the particular medication stored in the Static Memory [51]; i.e. where the unit being examined is the "Wrong Medication" [151]. This failure may arise from several disparate causes with linked disparate corrective handling procedures. For example, if the medication can be determined to be broken [153], then the broken unit can be discarded, a new unit issued, the unit count in the Storage Volume [5] appropriately decremented (by two, one for the discarded and one for the valid unit), the patient alerted to the change and the problem and solution logged into the treatment regimen record.

Or if the medication is the wrong strength [155], then the Operations Cap [1] can recalculate the unit count per dose for this dose using this specific unit, correct the issue for this dose (issuing further units if more strength is needed, requiring the return into the container [3] if too many were issued), recalculate the number of doses remaining in the container, notify the provider through the Remote Link [195] that this unit of the wrong strength had been placed into the container [3], and the problem and solution logged into the treatment regimen record.

Or if the medication is the wrong drug [157], then the Operations Cap [1] can discard the unit, issue a new unit, the unit count in the Storage Volume [5] appropriately decremented (by two, one for the discarded and one for the valid unit), the patient alerted to the change and the problem and solution logged into the treatment regimen record.

A second class of exceptions will be when at least one unit of a specific dose is returned by the user [161]. The Operations Cap [1] will, for all of these, log the return (as exemplified in FIG. 9); but the handling may differ according to the reason for the return. If the unit is unusable [163] then the Operations Cap [1] can discard the unit, issue a new unit, decrement the unit count in the storage volume [5] appropriately (by two, one for the discarded and one for the valid unit), alert the patient to the change and record both the problem and solution into the treatment regimen record, without changing the ordinal dose count.

If, however, the return is because the user indicates that internal symptoms he is experiencing deter or even prevent him from taking this dose [165], then the Operations Cap [1] will return the unit to the Storage Volume [5], correct (by incrementing according to the number of units) both the ordinal dose, and the unit count, recalculate the doses remaining in the container [3], notify the prescriber of the reported symptom(s) (which may optionally include readings from one or more medical testing devices (not claimed) supporting such symptom(s), and record both the problem and solution into the treatment regimen record.

If, in a third alternative possibility, the return is because the user indicates that one or more external constraints require that he not take this dose [167], then the Operations Cap [1] will return the unit to the Storage Volume [5], correct (by incrementing according to the number of units) both the ordinal dose, and the unit count, recalculate the doses remaining in the container [3], reset the next dose interval, optionally notify the prescriber through the Remote Link [195] of the reported symptom(s) (which may optionally include readings from one or more external devices (not claimed) establishing the external constraint, and record both the problem and solution into the treatment regimen record.

Because the Operations Cap [1] comprises both Static Memory [51] and a Control Set [19] it can be reprogrammed by an authorized individual to implement any devised set of exception-, correction-, and treatment-altering handling procedures, thereby enabling an adaptive and improving response to the complexities of the ongoing treatment regimen as experienced. The above set of exception handling routines can be modified through the Control Set [19] or the Remote Link [195] by anyone passing the fourth feedback checkpoint [8] of establishing authorization.

Figure 13:
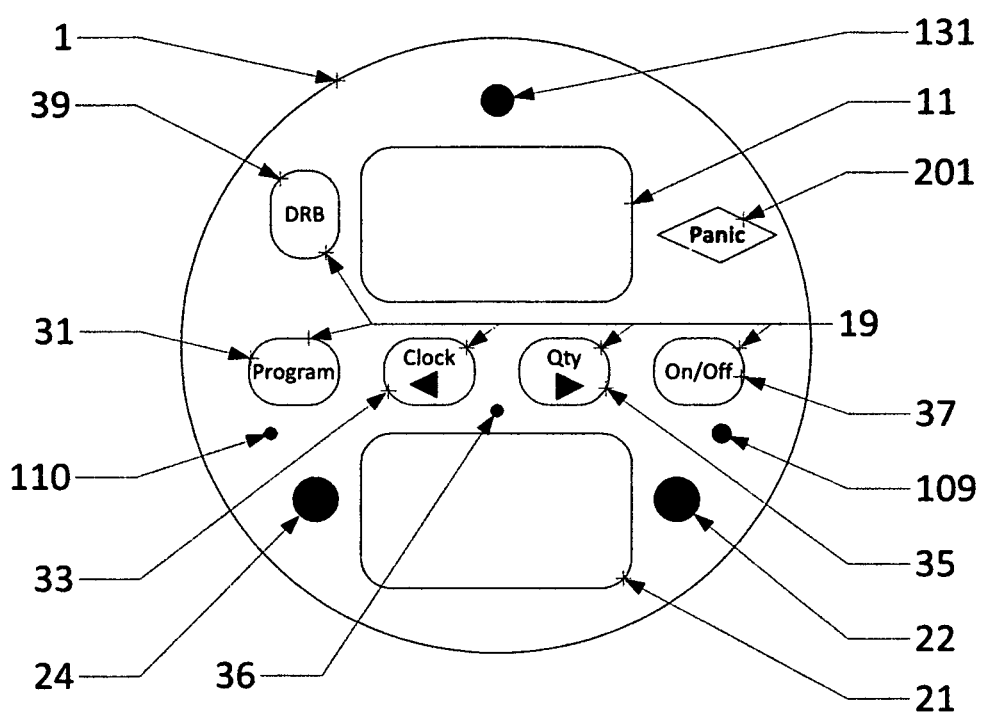
FIG. 13 is a drawing showing another and further embodiment of the Operating Cap [1] where it further comprises a Panic Button [201] the user may intentionally activate.

FIG. 13 is a drawing showing another and further embodiment where the Operating Cap [1] further comprises a Panic Button [201] that may be activated intentionally by the user.

FIG. 14, the drawing emphasizing the functional compartmentalization of an advanced embodiment of the invention wherein the container, with the Operations Cap [1] at one end, and a Battery Compartment [213] at the opposite end, comprises both a Storage Volume [5] for the individual units of the medication which will be delivered to the patient as all (or the summed parts) of each dose, and a Reject Storage Volume [211] for individual units of the medication which either during filling, or during use, have been rejected. The Reject Storage Volume [211] is connected to a filling and returning Dose Checking tunnel [7, 159] with Diversion Tubes [43, 146] whose openable, closeable, and latchable gates [45, 145] are connected to and controlled by the Operations Cap [1].

At the top of the drawing is the filling Dose Checking Tunnel [7] with its distal Counting Sensor [41], Identifying Sensor [42], Diversion Door [45], medial Counting Sensor [43], distal Filling door [11] (past which has been inserted a sizing insert [151]) and medial Filling door [13].

Near the bottom of the drawing is the delivery Dose Checking Tunnel [159], with its own distal Counting Sensor [177], Identifying Sensor [172], medial Counting Sensor [175], distal Filling door [161] and medial Filling door [163], and delivery Diversion Door [145] connecting the delivery Dose Checking Tunnel [159] to the delivery Diversion Tube [146]. In this embodiment, a dose comprising one or more units is taken from the Storage Volume [5], scanned-checked-and-counted through the delivery Dose Checking Tunnel [159] and passed into the Delivery Element [171] which is closed by the Delivery Gate [181]. In a further embodiment the Delivery Element [171] also has a MedPresent sensor [176] described below.

There is also a Return Button [173] on the exterior of the container [3] near the Delivery Gate [181], connected to the Operations Cap [1] and battery, by which the user can open the distal delivery Filling Door [161] to return from the Delivery Element [171] medication to the delivery Dose Checking Tunnel [159], allowing the user to return a unit which, when returned, depending on whether it is acceptable or has been rejected, can be placed in the desired storage volume.

Principle Elements of the Invention

As with the prior art, in the present invention incorporates at least one container [3] in which a patient's medication is kept for the patient's use. This container [3] comprises at least one Storage Volume [5], an Operations Cap [1], a distal Filling Door [11], a Dose Checking Tunnel [7], a medial Filling Door [13], a Battery Compartment [213], into which a battery (not claimed) to power the invention is placed, and in a further embodiment, a Delivery Element [171], all of which are connected and responsive with and to control, audio and visual elements described further herein. In the simpler embodiment the distal Filling Door [11] also serves as the latching closure and the Dose Checking Tunnel [7] as the Delivery Element [171] for removing pills from the Storage Volume [5]. Unless specifically stated otherwise, each door, or gate, not only is both connected with and controlled by the Operations Cap [1], but also is a door-plus-sensor combination.

The container [3] may be a regular container (e.g. a pill vial or bottle) specifically adapted to serve as the Storage Volume [5] and to operate with the Operations Cap [1], distal Filling Door [11], Dose Checking Tunnel [7] (a 'container/cap combination'), and in a further embodiment, Delivery Element [171]; or may be an integrated unit. The container/cap combination may be some form of pill cap, a multi-compartment pillbox, a salve-tube cap, a syringe carousel, an inhaler, a pump dispenser, a drop dispenser and the like. Those of skill in the art will understand, upon reading this description, that the container/cap combination can be used with any medication delivery system and with any type of medication, regardless of its form or dosage. The Operations Cap [1], Distal Filling Door [11], Dose Checking Tunnel [7], medial Filling Door [11] and Delivery Element [171] may be fully or partially removable or fully or partially openable, or may be an integral part of the container [3] through which medication is dispensed. While a particular connector (for connecting caps to containers) is shown, those skilled in the art will realize and understand that the actual mechanical interlock mechanism (e.g., screw, bayonet mount, snap-on, etc.) used will depend on the size and kind of container as well as its interlock system. In some embodiments, an adaptor may be provided to allow caps for one kind of container to fit on another kind of container. When the Operations Cap [1] is not an integral part of the container [3] but is added on, the preferred embodiment has at the medial interior end of the Operations Cap [1] a Sealed Connection Sensor [29], which registers that the Operations Cap [1] is both correctly and connectedly affixed to the container [3].

The Control Set [19] will be connected with the battery, each of the individual buttons which comprise it (in the preferred embodiment, a Program button [31], a Clock button [33] (which has a secondary function of a count decrementor), a Quantity button [35] (which has a secondary function of a count incrementor), an On/Off button [37], and a Dosing Release button [39]), any and all of the latchable and openable doors (including the Distal Filling Doors [11, 161], Medial Filling Doors [13, 163], Diversion Doors [45, 145], the Delivery Gate [181], and the Reject Door [212]).

In a further embodiment for visually-impaired users (the audio-enhanced embodiment), the container further comprises an Audio Element connected to the Operations Cap [1] and battery, said Audio Element further comprising a speaker [109] and a microphone [110] (for audio output and input, respectively) and the "ON/OFF" control button [37] and a "RECORD" button [26], functionally connected to the Operations Cap [1] and more specifically its microprocessor [52], dynamic memory [53], and Static Memory [51].

In the preferred embodiment, where each unit is separately checked in filling and in dispensation, the Storage Volume [5] is also connected to a lower medial Filling Door [161] at one location that is latchably openable and closeable and leads to a second (delivery) Dose Checking Tunnel [159] (which is like to the first, having a medial and distal ends, interior medial [173] and distal [175] counting sensors and unit identifying sensor [171], and motivation means), and through that, to the Delivery Element [171], and in the preferred embodiment, a Reject Access Door [177] to the Reject Storage Volume [211].

The Delivery Element [171], connected and outside the second Dose Checking Tunnel's [159] distal end and distal latching door [173], from which it receives each pill, comprises a Holding Volume [172] and a Delivery Gate [181] at the connection between Holding Volume [172] and the exterior of the container [3].

Each of the lower medial Delivery Door [161], Delivery Gate [181], and Reject Access Door [177] further comprise a locking mechanism using a solenoid controlled by the Operations Cap [1], that prohibits passage through that specific checkpoint unless and except as authorized by the Operations Cap [1]. For example, if no 'fill authorization' has been provided, the medial Filling Door [13] will remain closed and not permit the introduction of any pill into the Storage Volume; while if no 'dose delivery authorization' has been provided, the medial Delivery Door [161] of the second Dose Checking Tunnel [159] will not permit either the introduction of any pill from the Dose Checking Tunnel [7] into the Holding Volume [172] and the distal Delivery door (which may also be the Delivery Gate [181]) will not permit the release of any pill in the Delivery Element [171] to the exterior of the container [3].

In a first further embodiment, the Delivery Element [171] further comprises a MedPresent Sensor [176] connected to said Operations Cap [1], located within the interior of and preferably at the interior surface of the Holding Volume [172] for detecting the presence of a pill within the Holding Volume [172].

In a second further embodiment, the Delivery Element [171] further comprises a Return Button [173], connected to said Operations Cap [1] that will effect movement of the contents of the Delivery Element [171] back through the second Dosing Checking Tunnel back into any of the set of the storage volume and the Reject Storage Volume, depending on whether the returned unit matches, or fails to match, the pattern(s) identifying it as the specified medication.

In a distinct and third further embodiment, the Delivery Gate [181] will not permit moving the contents of the Delivery Element [171] by the Return Button [173] back into the delivery Dose Checking Tunnel [159], without authorization and recording of the action effected through the Operations Cap [1], whether said authorization comes from the patient using the Control Set [19] or the prescriber and/or provider using a Remote Link [195] which is also connected to the Operations Cap [1] and battery.

The Operations Cap [1] will be connected to the distal Filling Door [11], Dose Checking Tunnel [7], medial Filing Door [13] and Delivery Element [171], and will govern their action(s) (and in the further embodiment, the delivery Dose Checking Tunnel [159] and its sub-elements). The Operations Cap [1] further comprises a Control Set [19], a Visual Display [21], and at least one red [22] and one green light [24] (for visual output). The preferred embodiment has a liquid-crystal Visual Display [21], & the lights are LEDs.

The container further comprises a battery that powers the invention, including without being limited to an Operations Cap [1], Dose Checking Tunnel [7], Delivery Element [171], Visual Display [21], set of lights [22, 24], and Control Set [19] (and in the further embodiment, the second Dose Checking Tunnel [159]). This battery is located in its own separate Battery Compartment [213] of the container [3] and is configured any of its interior and exterior surfaces to both contain clear indication of the positive and negative terminal locations for the battery and to enable easy and direct access thus ease of replacement thereof.

The Operations Cap [1] effects the active operation of the invention; comprising, in the preferred embodiment, at least one printed circuit board [49] further comprising at least any of a microprocessor, microcontroller or embedded controller [52], both Static Memory [51] and dynamic memory [53], all used to store and run operational program(s) and data, and all connected through any of a bus, baseplane, and backplane to the Control Set [19], and to the battery.

The Control Set [19] is a set of buttons comprising operational, input, and programming controls for the invention. In the preferred embodiment these comprise a Program button [31], a Clock button [33] (which has a secondary function of a count decrementor), a Quantity button [35] (which has a secondary function of a count incrementor), an On/Off button [37], and a Dosing Release button [39]. Pressing the Dosing Release button [39] will start the process of delivering a dose from the Storage Volume [5] to the Delivery Element [171], as described in FIG. 8; in a further embodiment, this may require first meeting the validation process (described in FIG. 11).

The Control Set [19] will be connected with any of the latchable doors and gates within the container [3], excluding the cover to the Battery Compartment [213].

The invention further comprises a Clock [55] which may be part of or connected with any set of the Operations Cap [1], the Delivery Element [171], and any Dose Checking Tunnel [7, 159]. In the preferred embodiment the Clock [55] is part of the Operations Cap [1] and is connected with all of the above as well as the Control Set [19] and Visual Display [21], and receives power from the battery.

The Operations Cap [1] controls the operation of the invention, with the microprocessor [52] connecting to each of Static Memory [51] and dynamic memory [53], and being also connected with and programmed to combine with the Clock [55] to create both a timer and alarm which can be programmed with at least an alert for each dose time, or in an alternative embodiment, being connected with a separate timer subject to the Operations Cap [1]. When a time has come for a dose to be taken, the Operations Cap [1] activates any set of the Visual Display [21], red and green lights, and in the audio-enhanced embodiment the Audio Element's speaker [109] with a playback of a message recorded in the Static Memory [51] to serve as an alarm to the user that a dose should, or may, now be taken. This message may be recorded on the Static Memory [51] or retrieved through a Remote Link [195] (described further below); and it may be any of a set of different sounds, sound patterns, and/or volumes for different circumstances (e.g., a patient forgetting to take medication, lack of connectivity through the Remote Link [195], or sound of increasing intensity the longer a patient fails to take a medication dose within a dosing window. The sound may even be a voice alert from a trusted source, e.g., patient's voice, family member's voice, and/or prescriber's (doctor's) or provider's (pharmacist's) voice.

In a further embodiment the Operations Cap [1] further comprises a speech synthesizer [221], connected to the microprocessor [52], for converting a message retrieved from a source by the microprocessor [52] and placed into either Static Memory [51] or dynamic memory [53], from a first format into an audibly perceptible message format for subsequent presentation to the patient, wherein the microprocessor [52] is configured, upon determining based upon a reading from the Clock [55] that a predetermined time has arisen, to retrieve the message from the source and provide the message to the speech synthesizer [221] and play that message through the speaker [109].

In another further embodiment the Operations Cap [1] incorporates both a Remote Link [195] and in any of its embedded hardware, firmware, or static and dynamic memories, an open or other application programming interface (API) for itself. This may allow other devices and systems (e.g., remote computer, portable device, and/or a mobile wireless communications instrument to communicate with the container [3] through the Operations Cap [1] in a more efficient and user-friendly manner.

The invention preferably includes a "store and forward" architecture to ensure data collected and stored on its Static Memory [51] resides in that physical location if an upload network connection is not possible for some period of time.

The Visual Display [21] is preferably monochrome and can comprise any of a fixed set of glyphs, a segmented display, as is common in the realm of low cost liquid crystal displays, or a dot-matrix display if and as the displayed content may be a 2D bar-code, thus enabling it to also function as a machine-readable information display. The Visual Display [21] may provide other useful information, e.g., an indication of whether a dose has been placed in the Delivery Element [171], and may optionally indicate a schedule of past or future dose times as text (e.g. "2:40 pm") or as a graphic portraying an analog clockface. The Visual Display [21] may also display other information such as instructions as to external and internal constraints on taking a dose, unit count for a dose, active ingredient (medicine) name, battery level, time, network connectivity strength (if RF connectivity is also embedded in the cap), any set of names for prescriber, provider, and patient, availability of rewards, financial incentives, social network status, who the data is shared with or other such medically relevant information.

The prior art failed to track not just whether or not a dose is removed from the container, but also whether that dose is replaced, rejected, or flawed (and thus becomes a deviation from the plan). The present invention will when and as possible, correct such deviations within the predetermined constraints, or if such is unfeasible, modifying the on-going treatment plan to adapt to such deviation(s), and record each deviation between plan and regimen, prescription and reality. Accordingly in a further embodiment of the invention, the container further comprises a Reject Storage Volume that will store doses (or parts thereof) that have been rejected, either by the invention (e.g. for not being a correct unit of the desired medication) or the patient (for a reason the user may and should—but might not—provide). The Reject Storage Volume [211] is not connected to the Storage Volume but as described below to the Dose Transport and Inspection Tunnel.

The Dose Checking Tunnel [7] is connected at its medial end to the Storage Volume [5], further comprises a Medial Counting Sensor [43], Identifying Sensor [42], and Distal Counting Sensor [41] placed both at the interior wall (in or just above its interior surface with unobstructed access to the anterior of the Dose Checking Tunnel [7]) and in that sequence between its medial to distal ends, and means to move each unit from one end to the other. In the preferred embodiment of the invention each of the Medial Counting Sensor [43] and Distal Counting Sensor [41] is an optical sensor, such as a low-power photodiode (see FIG. 4). Upon receiving a command from the Operations Cap [1], the medial Filling Door [13] at the medial end of the Dose Checking Tunnel [7] is unlatched to allow a single unit of the stored medication to move from the Storage Volume [5] into the medial end of the Dose Checking Tunnel [7], and then, subject to its successfully being inspected and identified, out the distal end (a further embodiment has a separate Dose Checking Tunnel [7] for both filling and delivering; in this, the single unit passes through the distal Filling Door [13] into a Delivery Element [171]).

Each unit of each dose (each pill) is checked as it is being made available to the user and is passing through the Dose Checking Tunnel [7]. At least one Identifying Sensor [42] (in the preferred embodiment, a camera) evaluates whether this specific, particular unit meets the sensory pattern for that particular medication. For each unit, the distinguishing physical characteristic(s) (which may be any combination of the set of shape, weight, size, color, or the presence/absence/difference of identifying symbol or 'tag', or specific reactivity to light or electrical stimulus—including phosphorescence or lack thereof upon illumination by specific wavelength(s) of light, specific reactivity to hardness, or sonic testing) are tested and if not matched against the recorded pattern for that medication, that unit is flagged to be discarded rather than dispensed and a record of that deviation (including time, cause, and action resulting from it) is made and stored in the invention. In the preferred embodiment the Identifying Sensor is a 2D/3D CCD camera, connected to the Operations Cap

[1], that takes an image of the unit, which then is compared against the pattern (any of a set of stored images for that specific medication, at the intended concentration and volume) stored in the Static Memory [51]. To best enable the imaging and comparison the interior wall of the Dose Checking Tunnel [7] is a featureless, smooth, matte black colored, and low reflection material.

In a further embodiment, to accommodate different sized and shaped units, an insert specifically sized and shaped for the intended and particular medication unit (pill) may be fitted inside the Dose Checking Tunnel [7], with each said insert both so configured as to allow unobstructed sensing of each of the Medial Counting Sensor [43], Identifying Sensor [42], and Distal Counting Sensor [41], and also having its interior wall a featureless, smooth, matte black colored, and low reflection material. (See FIG. 16.)

(A like detailing, above and below, should be read here for the whole and comprising elements of the delivery Dose Checking Tunnel [159].)

As can be understood from the above detailed explanation, in the preferred embodiment the present invention provides for bidirectional detection—of medication going out to the patient and being returned by the patient—at each dosage instance, instead of presuming unidirectional flow of each and every dose of medication from the provider to the container and next through to the user.

One key part to this bidirectional detection is the pair of sensors offset so that movement of a dose in the outward vector is differentiated from motion of a dose in the inward vector. In the preferred embodiment the passage of a pill by the Medial Counting Sensor [43] first and the Distal Counting Sensor [41] second is an 'outward' passage, while that of a pill by the Distal Counting Sensor [41] first and the Medial Counting Sensor [43] second is an 'inward' dose.

In a further embodiment there is a both a Reject Storage Volume [211] for 'rejected' or 'wrong' units and a separate Rejects Gate [45] controlled by the Operations Cap [1] connecting the Dose Checking Tunnel [7] to the Reject Storage Volume [5], and in that embodiment the rejected unit (pill) is sent there instead. (See FIG. 4, 15.) This effects separation of broken, or detectably adulterated, units, of the 'wrong' and unintended medication, and prevents the prior art's error of presumptive dispensing despite differentiation between what was provisioned and what was prescribed. The unique indicia checked for by the Identifying Sensor [42] may include visible characteristics including color, size, shape, inscriptions thereon, etc.; and this 'recognition element' such as an optical scanner is connected either locally or through the Remote Link [195] configured with at least one locally contained or external data base having general medication identification data and optionally patient-specific information to scan and identify the medication (and optionally the dosage, specific formulations, manufacturing source, etc.) and to record and correlate information regarding patient medication usage.

In a further embodiment of the invention, any Dose Checking Tunnel [7, 159] is flexible and is wrapped in an electromagnetically-driven coil [51] which will compress from one end to the other according to the charge fed into that electromagnetically-driven coil [51], such that when a pill must be moved from the medial end towards or to the distal end, the electromagnetically-driven coil [51] compresses behind the pill at the medial end and then the wave of compression moves along the wire and down the Dose Checking Tunnel [7, 159] to the distal end; and when a pill must be moved from the distal end towards or to the medial end, the electromagnetically-driven coil [51] compresses behind the pill at the distal end and then the wave of compression moves along the wire and up the Dose Checking Tunnel [7, 159] to the medial end.

In yet a further embodiment of the invention the Dose Checking Tunnel [7] further comprises a third, latching, Reject Gate [45] (which in turn is connected to the Operations Cap [1]) (see FIG. 4) that controls the opening to a secondary tunnel [46] connecting the Dose Checking Tunnel [7] to the Reject Storage Volume [211]. This Reject Gate [45] is opened whenever a unit is inspected and either (a) does not match the identifying pattern for the correct medication; or (b) has been returned by the user through the Delivery Gate [181] and identified by the user as being no longer suitable for assimilation, thereby allowing the rejected unit to pass through a one-way latching gate [177] at the far end of the second Dose Checking Tunnel [159] into the Reject Storage Volume [211]. In yet a further embodiment a Clearance Gate [212] can be activated by an authorized prescriber or provider to access from the outside the Reject Storage Volume [211] and thus enable emptying out, and inspection and or counting, of any and all rejected units retained within the Reject Storage Volume [211].

The invention checks each pill before it is delivered to the user as all or part of a single dose, by passing that pill by the Identifying Sensor [42] which examines that pill and compares the relevant data against the stored (and thus known) validating pattern for that specific medication. In the preferred embodiment this is a visual sensor, though the identifying sensor may comprise and use any one or more of visual, mass, RFID, Near-Field-Communication ('NFC'), odorant, chemical composition, sound, conductivity, or other sensors that can differentiate pills by any of shape, engraving label, size, color(s), image, pattern, scent, reactivity, vibratory, or magnetic or electrical response, i.e. any fixed and determinable, uniquely identifying physical characteristic(s) of the pill. In the preferred embodiment this Identifying Sensor [42] serves a dual function because by being placed between the Medial Counting Sensor [43] and the Distal Counting Sensor [41], it allows each pill to be checked as it is passed out to, or replaced back in by, the user.

In a further embodiment the invention allows inspection of each unit as it is placed into the container [3] before it is put into the Storage Volume [5] to capture and correct provider errors while the container is being filled, whereby a mistake by the provider that places a wrong unit into the distal Filling Door [11] can be captured and corrected (by routing that wrong unit to the Reject Storage Volume [211] as described above) while the container is being filled. If the Identifying Sensor [42] detects a pill which cannot be positively identified as a unit of the prescribed medication (i.e. the shape, color, mass, surface pattern, etc. are wrong) then the filling may be flawed and thus must be stopped and corrected, so the Operations Cap [1] locks the medial Filling Door [13] closed, activates an alarm (audible or visual or both), locks the distal Filling Door [11] open, and optionally also records and/or sends a message to the provider and optionally also the prescriber is sent, to prevent a mistake such as placing two distinct types of medication into an interior storage meant to hold just one specific type.

In yet another and further embodiment the invention further comprises a second Dose Checking Tunnel [159] connecting the Storage Volume [5] with the Delivery Element [171], that allows the user to reject a specific unit and return it with the Return Element [173], whereby the invention determines whether that returned unit is acceptable and can be returned to the Storage Volume [5] or is unacceptable and must be placed in the Reject Storage Volume [211].

In a further embodiment the invention further comprises an authentication and validation element (security check) which uses any of a PIN-code, bio-data sensor and stored identifying pattern for the set of individuals who are authorized to issue exceptions to specific and identified external and internal constraints and thus permit an over- or under-dose, to be taken by the patient and recorded as a variation from the treatment plan within the treatment regimen, with the nature of the exception, the authorization requirement, the authorization matching, and the fact of that variation in dosing, all recorded and reported to the prescriber and/or provider. In yet a further embodiment the Remote Link [195] can be used by any of the prescriber and provider to override the Delivery Element [171] remotely to effect a lock preventing any delivery of any unit(s) of the medication, to control attempted overdosing by the patient.

In like fashion, upon receipt of information indicating a necessity for an exception, the Remote Link [195] can be used by any of the prescriber and provider to override the Operations Cap [1], Dose Checking Tunnel [7], and Delivery Gate [181] and to effect delivery of any unit(s) of the medication in response to an emergency need by the patient for a further issuance of the medication beyond the limits of the treatment plan, with said authorization and delivery being recorded in the treatment regimen automatically as effected.

As part of the treatment plan the total count of the units of medication placed inside the Storage Volume and the date, time, and individual provider performing such placement are recorded in the Static Memory [51]. As part of validation of each unit and dose, the invention compares any input data (e.g. from an external record or the treatment plan) establishing the 'use-by' date for its contents and, if the Clock [55] establishes that such a date has been reached, alerts all of the patient, prescriber, and provider to the necessity to (a) remove for destruction rather than use all remaining units inside the container, and (b) replace the contents of the Storage Volume with currently-valid units of the same medication for the ongoing progress of both treatment plan and treatment regimen. If the invention has been appropriately programmed it may also issue one (or more, in series) refill request to any of prescriber and provider, within the authorizations of the number and timing (minimum and maximum bounds) of refills for that patient for that medication.

Between one dose and the next scheduled in the treatment plan, there may occur any of a set of constraint violations. This will be a greater concern when the user has more freedom to choose any set of the timing and strength of a dose, for while the most local constraint (e.g. '4 hours between doses') may not be violated, a larger scope constraint may be violated ('no more than 4 doses in 24 hours'). If a medication must be kept above or below a certain temperature to remain effective (unfrozen, or chilled), then too much time in the wrong environment may spoil the medication. Or a medication may reach its shelf life; or a renewal must be ordered to ensure sufficient supply before the next dose. In a further embodiment, depending upon the limitations of programming and Static Memory [51], the invention's Static Memory [51] may be provided with and retain details of the medication including the local and broader constraints, environmental constraints, and any set of expiration date, dosage level, name of the drug (both common and trade name) as well as an indication if it is a generic version, the number of refills and the number of remaining refills on a prescription, whether there is duplication, prescribing doctor(s), pharmacist or other health professional, common side effects and interactions with other drugs and food, how and when to take the dosages and the ability to receive medication alerts from the Web or Internet.

Accordingly, in some embodiments, the invention is able to alert any set of the patient, prescriber, provider, or designated contact for the contents in the Storage Volume [5] to be discarded or replaced using any of the alert mechanisms described above and/or other alert(s). Such information stored in the Static Memory [51] is also preferably accessible for updating which may be done by any authorized and validated individual, be that the patient or more preferably by the dispensing pharmacy (provider), physician or other health professional (prescriber) aware of the changed information. Additional information which may be stored in the Static Memory [51] may include contact information for any of the prescriber and provider, and the entire record(s) of the usage of the container, including all medications, treatment plans, treatment regimens (and most specifically, all inputs relating to the external conditions, internal conditions, and variations between plan and experienced regimen) as these can and should govern full, knowing evaluation of the efficacy for that patient for that medication and that treatment plan.

A count is kept of the unit(s) for each dose, and that count is measured against the constraint(s) of the treatment regimen upon passing the Medial Counting Sensor [43] and then Distal Counting Sensor [41] in an outward direction. In a further embodiment, if the count would violate the upper limit, the invention does not allow the passage of that or any unit past the Distal Counting Sensor [41] and through to the Delivery Element [171] unless, except and until a specific authorization is received from the provider, at which time the issuance of both authorization and overcount/overdose is recorded and stored by the invention as a deviation from the treatment plan.

If enough units have passed the Distal Counting Sensor [41] but the patient takes too few units out of the Delivery Element [171] to comprise a dose—i.e. if there are units left in the Delivery Element [171] after the 'timing window' has passed—then a further alarm is activated alerting the user; and, if the unit(s) remaining in the Delivery Element [171] is(are) not taken within the existing 'dosing window', the undercount and underdose is recorded, the deviation is reported to the provider, any adjustment to the provisioning schedule is computed and then made, and either the counted but not dispensed unit(s) is(are) returned past the Medial Counting Sensor [43], counted back into the Storage Volume [5] and decremented from the record of units dispensed, or the per-dose count of units for the next dose is decremented by the number of units remaining in the Delivery Element [171] and the Delivery Gate [181] is latched until the next release time.

Additionally, each dose is checked against the constraints governing its proper dispensation to this user at this time under the conditions set by the treatment regimen. These constraints may be referenced from an external source (e.g. a digital storage of the Physicians Desk Reference, or that medicine's producer's private data records) or may be stored in the invention's memory. If a dose would result in the user taking an overdose, that would be recorded and an immediate alert sent to the provider and prescriber and, without receipt of an authorization, would not permit that dose to issue through not letting the units pass into the Delivery Element [171] but keeping them in the Dose Checking Tunnel [7].

The invention will also indicate to the user what the medication is which is being dispense, basing its determination on the sensor(s) and prior records of inbound medication. In the preferred embodiment notification will be provided on a container-centric LCD display and will show any of the name(s), dosage, and unit counts for that medication for that patient for this specific delivery.

And as different medications may require different delivery efforts, a set of differing inserts [151] that will match the bulk retention volumes for each specific medication, to the Dose Checking Tunnel [7], can be provided for the user as described above. The selection of the correct insert [151] will be enabled only when the treatment plan authorizes the delivery of a dose, or upon paring of a specific request of the user and authorization of the provider (provided in advance, with constraints on number of times, minimal intervals between requests, maximum number of total approvals in any or multiple interval scalars), is tested and recorded as being satisfied by the invention, which then deactivates the blocking element from preventing that insert [151] matching up to the Dose Checking Tunnel [7].

If a dose is removed and not replaced, the invention will log that dose and time, unless and except as the user may enter a correction. If, for example, the dose comprises three pills and three pills were removed, the invention would record that 3 pills were taken. If the user drops one pill and does not wish to take that specific, but now-contaminated pill, the user may enter a correction. In that further embodiment the user inserts the rejected pill back into the Dose Checking Tunnel [7], where the rejected pill is sensed passing inwards of the Distal Counting Sensor [41] and checked by the Identifying Sensor [14]. If the inserted unit does not match the user is alerted to this (thus preventing subversion by intentional substitution) and the count of dispensed units is not altered; while if the unit does match the count is decremented and the unit is returned to the container, possibly for re-release later. In a further embodiment, the user has the option to have the unwanted and untakeable pill diverted into a Rejected Storage [211] where it will be counted and stored.

Both the issuance and the correction are recorded in the Static Memory [51] and that record of deviation from the treatment regimen is delivered to the provider at the next review. In a further embodiment of the invention the provider may query the invention about the absence, or presence and nature of, any deviations at the provider's initiative, and thus detect whether grounds exist for an expedited review (perhaps to catch significant under- or over-dosage problems before too much harm can arise) or change in the treatment plan based on the patient's experienced treatment regimen.

In the event that any of the unit count, medication identification, timing or other constraint, indicate that this dose should not be taken by the user, the invention provides an alert specifying the cause for the alert and records the attempt to access that specific medication. This attempted deviation is used by the preferred embodiment as an impelling cause to effect communication to the prescriber and to the user as to both the attempt, and nature, of the violation. In the preferred embodiment the prescriber can authorize the release, in which case both the record of the deviation and authorization for release are made and stored by the invention.

For the purposes of the following descriptions of the functioning of the invention, it will be described as for a container holding one or more pills, though different containers for handling liquid, injectable, 'patch', and insertable medications are also both feasible and described in the present art. Time will be given in a 24-hour clock format to avoid confusion between 'a.m.', and 'p.m.' or indeterminate or duplicate counts) "12:00"; noon or midnight).

Exemplar of Operation

In this principle exemplar a user has consulted a doctor (the prescriber) and from that prescriber received a treatment plan for a specific medication (a standard statin) to be taken in a given structure sufficient to establish and maintain a working level of the active ingredient in the patient's bloodstream 24 hours a day, with a start date and no end period specified. (I.e. the condition is deemed chronic and continuing.) Alone or working with a pharmacist (the provider) the prescriber determines that the medication comes in units having enough active ingredient each to require each single dose to be '1 pill'; with external constraints requiring that any dose be offset at least 1 hour before or 2 hours after a meal, and requiring a separation between doses of 4-8 hours if the patient is awake and 6-12 hours if asleep; and limiting the number of doses a day to a maximum of 3 doses. Prescriber, provider and patient agree that a '10 minute' timing window provides sufficient, sustainable accuracy without affecting the working level of the medication in the patient's system. The provider delivered to the patient the invention pre-filled for a thirty-day (one month) period, ten days past, so the treatment regimen is about to start its eleventh day.

The patient, having taken her last dose for the tenth day at 22:00 and then gone to bed and stayed asleep, awakens at 06:00 and eats breakfast at 07:30. Although the patient could have taken a dose in the first half-hour after waking (an hour before the meal), she failed to do so. Having been asleep, her next dose must be put off to no sooner than 09:30 (two hours after eating) yet be taken no later than 10:00 (twelve hours after her last dose). The patient sits down to digest her breakfast and begins to watch television ("Days of Our Lives", in rerun).

The invention sounds an availability alert at 09:25, moving one pill out of its storage volume into its dosage transport and identification tunnel towards the dispensing outlet, and verifies with the identifying sensor therein that this pill matches the pattern for the scheduled and prescribed medication (being mauve in color, CMYK-scale (12, 31, 0, 0) and oval, as described in the CDC's and pharmaceutical providers' respective descriptive references, the pattern in the invention's Static Memory which is compared against the identifying sensor's image).

At 10:00 a.m. the patient has failed to activate the delivery element and remove the pill from the dispensing outlet. The invention activates its localized (on-dispenser) visual and audible immediate alerts, a flashing red LED and short, loud, ping-tone. After a further five minutes without activation and removal, the invention activates again the localized alerts and sends out notifications per the treatment plan's direction (which in this case was the provider's standard fallback, immediate emails to each of patient and prescriber, and a text message to the patient's caregiver for that morning).

The patient responds at 10:10 (she had been delayed by trouble with the toilet). She can see both directly and at the visual display there is a pill at the delivery element, and confirms with a tap that she has not had a meal within the past two hours (she finished at 07:50). Having satisfied the external constraints, the invention releases the lock and the patient takes the first pill from the delivery element.

As she does, the invention recalibrates the treatment plan for the change (i.e. the delay). Her second daily dose now must move to a timing window between 14:05 and 18:15 (i.e. 14:10 offset five minutes early, and 18:10 offset five minutes late); and her third dose between 22:05 and 0:15 (just after midnight on the following date). The invention displays on its visual display the next two dose intervals and times for her to see. Seeing these, and knowing that lunch is served starting at 11:30 and dinner at 17:00, the patient decides to eat lunch as soon as it is served. Finishing by 11:55, she then takes her second dose at 14:06 (which is within the 10-minute 'timing window' of 14:10). Having taken the second dose without interruption or problem, her third dose is re-set to be taken between 18:00 (four hours, less a five-minute timing window overlap) and 22:11 (six hours plus a five minute timing window gap). After eating dinner early and finishing by 17:30, the patient comes in at 18:05. The invention has already passed and validated a first pill to the dispensing outlet, but when queried, the patient indicates that she has eaten within the past two hours. She is then prompted to and enters the time she finished eating, and the invention reschedules her third dose to between 19:25 (the minimum 2 hour offset from her last meal, with a five-minute timing window overlap) and 22:11 (the maximum 8 hour (plus five-minute timing window gap) range from her second dose). She comes in at 19:55, the third dose is delivered with validation, and the next day's schedule is set. Since the minimum time between any two doses (the four hour window), which would place the next dose at 23:55 and thus would violate the 3 doses within a day, the next dose is moved and set for anytime between 00:06 (so beyond the 'timing window' overlap of the 3-dose-max-per-day) and 09:55 (allowing the 12-hour, not 8-hour gap since she will be sleeping).

Alternative Sub-Courses

If the patient, unable to sleep, had tried to take the medication at 23:30, the invention would (a) not pass a pill through the dosage tunnel, and (b) give the reason, via any or both of the display and speaker (using a prerecorded message, e.g. "You have already taken 3 doses, the maximum allowed, this day", out of the Static Memory). Even if there were a pill remaining the in dispensing outlet, the door would not be unlocked.

If, instead, the medication had required sufficient concentration that each dose comprised '2 pills', each time that a dose came due the invention moves both a first and a second pill through the Dose Checking Tunnel [7] to the dispensing outlet, again checking and confirming with the identifying sensor between the Medial Counting Sensor [43] and Distal Counting Sensor [41] that each pill matches the pattern for the scheduled and prescribed medication. The patient removes both pills from the dispensing outlet; finds a glass of water, and takes both.

If a pill is left in the dispensing outlet, then the invention notifies the patient that she has not taken all of her medication. If the timing window passes and the second pill still has not been taken, then the dispensing outlet relocks (it will not unlock until the next dose is to be released), the undercount is recorded and the failure to take the full dose is sent to the prescriber, and the count for the number of pills to be sent from the storage container through the dosage tunnel is reduced, for the next dose only, from 2 to 1, to properly account for the (hopefully, temporarily) pill not taken.

Exception Handling

Anytime an external constraint (lack of or presence of food in the stomach; insufficient time interval; unacceptable air pollution levels, etc.) is experienced such that under the treatment plan a dose would not be permitted, a patient may initiate an exception request. This would be transmitted from the invention (preferably by the external devices as known in the prior art) to the prescriber for the prescriber's determination and, if an authorized medical professional, prescriber, or other person determines that the exception should be allowed and issues that permission, all of the request and permission are logged and the constraint is, for that dose only, removed as a barrier, and the dose will be allowed to be delivered to the patient. That permission would only be on record and effective for that specific, particular dose. Further intervention could see exceptions repeatedly granted or the treatment plan changed, but only with the supervision and explicit authorization of the qualified medical decisionmaker(s).

The preferred embodiment incorporates memory that records the treatment plan, the filling of the storage compartment(s), the dosage log (times, intervals, dates, units, and external constraints, for each specific medication; and all alerts, exceptions, and errors experienced in the treatment regimen), which records can be retrieved by anyone authorized (patient, provider, prescriber, or other person pursuant to HIPAA) to review the medical treatment ordered for and experienced by the patient. This record will form a daily, weekly, monthly, or other durative period log that can be sent to or retrieved by said authorized parties for more ready access and review through said links to external devices.

If the storage compartment is empty, or if the count of total units that have been dispensed falls below a set minimum, such that a refill of the medication must be requested before the remaining units are dispensed, then the preferred embodiment will send out an alert to each of the user, prescriber, and provider that a refill is necessary for the treatment plan and regimen to continue. In a further embodiment the notification will include the minimum number of doses and time remaining, and in yet a further embodiment the notification will include the maximum number of doses and time remaining, to best enable the patient, provider and prescriber to integrate the refill process with the current operational state of the treatment regimen.

In the preferred embodiment the storage container is only accessible when an authorized provider of the medication(s) in the treatment plan enters an unlocking code, and when the storage container is either (a) empty or (b) below the minimum stocking count as set forth in the treatment plan.

In a further embodiment of the invention, each unit of the medication that is fed into the invention passes through a input transfer tube (otherwise referenced as the Dose Checking Tunnel [7, 159] that contains a sensor capable of counting, and identifying, each unit and verifying that each specific unit is actually what is intended to be placed in the storage container, and is not a wrong medication, a broken unit, or a degraded unit.

Network and Remote Device Connection Capability

In a preferred embodiment, the cap also has network connectivity via its Remote Link [195], which implements any of the standard means (local RF or intermittently via physical connector) known to the prior art to connect the Operations Cap [1], and more specifically, its Control Set [19] and microprocessor [52] and Static Memory [51] to external computational and communication assets. The Remote Link [195] can use any of the multiple near-field wireless communications technologies (Wi-Fi, Bluetooth, NFC) to communicate with additional devices (Smartphones, tablets, portable computers, emergency alert bracelets and/or necklaces) that then are used to transmit information to the prescriber and provider; or in a further alternative has a hardware 'port' (e.g. any of the set of serial, parallel, universal serial bus ('USB'), micro-USB IrDA, Ethernet, RS-232, and standard telephone data ports) suitable for a wired link to any like-connectable device for such network communication. Firmware and software (an API, Application Program Interface) capable of operating, programming, and reprogramming the invention through these additional devices by standard remote linkages, as described and well known in the prior art, form part of the invention but are not claimed.

Manual Interaction and Intervention

The majority of alterations in the treatment plan can come automatically as the feedback from the user changes the dosage(s) taken; but changes can also be manually entered through the controls by an authorized human intervener. In the preferred embodiment of the invention a stacked set of pre-selected treatments, whose ordered hierarchy of members are matched to and will handle the majority of experienced contingencies, are stored in the Static Memory [51].

Additionally, specific alterations to the treatment plan can be individually entered by that authorized human intervener, either through direct entry through the controls, or by transmitting the pre-programmed commands through the remote linkage means.

Mobile Interaction and Intervention

Another source of alterations in the treatment plan may become necessary from the patient moving from one place to another place (whether just travelling, taking an extended vacation, or relocating the patient's home) when the geographic and temporal environment changes (i.e. the time zone and/or physical location change). In a further embodiment of the invention, a GPS connection is used to re-set both the time stored in the Static Memory [51], the Clock [55] (if different), and the treatment plan, with the duration from the last dose being held constant but the 'clock time' for the subsequent dosing schedule being readjusted to reflect the 'new, present' time. In a further embodiment of the invention, the GPS location of the invention is used by any of the user, prescriber, or provider to match up to the nearest pharmacy which can be authorized and does or will carry the required medication, to execute any necessary refills; and this information about the new provider is sent to each of the patient, prescriber, and old and new pharmacies. Similarly, a change in prescriber can be searched for and updated for all of the provider, new and old prescribers, and patient.

Emergency/Panic/Help Button

In a further embodiment of the invention there is either a combination of the Control Set [19] or a single, specific, visually and even tactilely differentiated Panic Button [201] that requires only a single, but sustained press (for at least 2 seconds, to avoid incidental and unintentional activations). When the Panic Button [201] is thus activated the invention uses an on-board physical location determiner (in the preferred embodiment, the GPS) to determine the physical location of the user and sends this location data and an emergency call-out to local emergency services; and in a further embodiment, the time of activation of the Panic Button.

The preferred embodiment will incorporate on-board encryption of data records of the treatment regimen to comply with Federal HIPAA regulations. It will also incorporate as part of the device label an embedded RFID chip and antenna (FIG. 14, [215]) to communicate all medication information from its content(s) to the authorized additional devices, in further compliance with Federal regulations.

The preferred embodiment of the invention will incorporate a microprocessor [52] and a set of sensors, memory, and power supply as described and well known in the prior art to detect filling of the storage container [3], directional movement of each individual unit through the Dose Checking Tunnel [7, 159], and to specifically identify each individual unit as belonging (or not) to the prescribed medication(s); as well as a display, audio and visual alert(s), LEDs (colored with at least two different colors to differentially alert the user) [22, 24], a set of operational and programming control buttons [19] to enable the different activities and interactions between the invention and the user; and in the preferred embodiment both a speaker [109] and microphone [110] to enable audio data transmission between memory and external prescriber/providers, and the individual patient (and user). In a further embodiment, additional memory or enhanced communication linkage with a remote support device will provide purely audio alerts and intercommunication for blind users of the invention, using any combination of pre-recorded, modal and state-determined, and live human voice prompts, queries and responses.

A further embodiment of the invention incorporates a placement sensor on the surface of the individual dosage unit with a short-range wireless link (such as an RFID chip specific to that dosage, or a sensor reactive to human-digestive-tract substances (e.g. any of saliva and stomach acid), where the absence of the signal (when the RFID chip is shielded from detection within the human alimentary system) or effecting burst (when the sensor encounters the triggering substance) indicates that the bearing dosage has in fact entered the patient's digestive system.

In yet a further embodiment the invention further comprises a solar power collection element (not shown), connected with the battery and the Operations Cap [1], for maintaining the minimal operating power necessary to operate the pattern-matching, recording, and dosage-delivering and retrieval efforts.

In yet another and further embodiment the invention further comprises at least one light source (not shown) providing sufficient illumination to enable night-time use independent of external light sources, providing such light source through any set of backlighting the display, illuminating the dosage retrieval area, illuminating the operating control(s), and illuminating a high-lumen LED.

While this invention has been described in reference to illustrative embodiments, this description is not to be construed in a limiting sense. Various modifications and combinations of the illustrative embodiments as well as other embodiments of the invention will be apparent to those skilled in the art upon referencing this disclosure. It is therefore intended this disclosure encompass any such modifications or embodiments.

The scope of this invention includes any combination of the elements from the different embodiments disclosed in this specification, and is not limited to the specifics of the preferred embodiment or any of the alternative embodiments mentioned above. Individual user configurations and embodiments of this invention may contain all, or less than all, of the elements disclosed in the specification according to the needs and desires of that user. The claims stated herein should be read as including those elements which are not necessary to the invention yet are in the prior art and are necessary to the overall function of that particular claim, and should be read as including, to the maximum extent permissible by law, known functional equivalents to the elements disclosed in the specification, even though those functional equivalents are not exhaustively detailed herein.

Although the present invention has been described chiefly in terms of the presently preferred embodiment, it is to be understood that the disclosure is not to be interpreted as limiting. Various alterations and modifications will no doubt become apparent to those skilled in the art after having read the above disclosure.

The various illustrative logical blocks, modules, and circuits described in connection with the embodiments disclosed herein and shown in the figures may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor [52], but in the alternative, the processor may be any processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration, and in one or more locations with intercommunication capabilities and linkages.

In one or more example embodiments, the functions, methods, and/or applications described may be implemented in hardware, software, or firmware executed on a processor, or any combination thereof. If implemented in software, the functions may be stored on or transmitted over as one or more instructions or code on a computer-readable medium or memory. Computer-readable media include both non-transitory computer storage media and communication media including any medium that facilitates transfer of a computer program. A storage medium may be any available media that can be accessed by a computer. By way of example, and not limitation, such computer-readable media can include non-transitory computer-readable media including RAM, ROM, EEPROM, CD-ROM or other optical disk storage, magnetic disk storage or other magnetic storage devices, or any other medium that can be used to carry or store desired program code in the form of instructions or data structures and that can be accessed by a computer. A computer-readable medium can include a communication signal path. For example, if the software is transmitted from a website, server, or other remote source using a coaxial cable, fiber optic cable, twisted pair, digital subscriber line (DSL), or wireless technologies such as infrared, radio, and microwave, then these coaxial cable, fiber optic cable, twisted pair, DSL, or wireless technologies such as infrared, radio, and microwave are included in the definition of medium.

The system may include various blocks or modules as discussed above and shown in the figures. As can be appreciated by one of ordinary skill in the art, each of the modules may include one or more of a variety of sub routines, procedures, definitional statements and macros. Each of the modules may be separately compiled and linked into a single executable program. Therefore, the description of each of the modules is used for convenience to describe the functionality of the disclosed embodiments. Thus, the processes that are undergone by each of the modules may be redistributed to one of the other modules, combined together in a single module, or made available in, for example, a shareable dynamic link library.

The invention may be used in connection with various operating systems such as Linux®, UNIX® or Microsoft Windows®. The operating instructions may be written in any conventional programming language such as C, C++, BASIC, Pascal, or Java, and ran under a conventional operating system. The operating instructions may also be written using interpreted languages such as Visual Basic (VB.NET), Perl, Python or Ruby. In addition, those skilled in the art also will appreciate that the various illustrative logical blocks, modules, circuits, and programs—actual embodiments of the steps and substeps of methods described in this document—may be implemented as electronic hardware, data processor software, or combination of both. To clearly illustrate this interchangeability of hardware and software, various illustrative and non-exclusive components, blocks, modules, circuits, and steps have been described in this document generally in terms of their functionality. Likewise, the various illustrative logical blocks, modules, and circuits described in connection with the system for medication management disclosed in this document may be implemented or performed with a general purpose data processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof, designed to perform the functions described in this document. A general-purpose processor may be a microprocessor [52], but in the alternative, the processor may be a conventional processor, controller, microcontroller, or state machine. A processor may also be implemented as a combination of computing devices such as, in a non-exclusive example, a combination of a DSP and a microprocessor [52], a plurality of microprocessor [52]s, one or more microprocessor [52]s in conjunction with a DSP core, or any other such configuration. Whether such functionality is implemented as hardware or software depends on the particular application and design constraints imposed on an overall system. Skilled artisans may implement the described functionality in varying ways for each particular application, but such implementation decisions should not be interpreted as causing a departure from the scope of the present invention.

It will be appreciated by those skilled in the art that various modifications and changes may be made without departing from the scope of the described technology. Such modifications and changes are intended to fall within the scope of the embodiments that are described. It will also be appreciated by those of skill in the art that features included in one embodiment are interchangeable with other embodiments; and that one or more features from a depicted embodiment can be included with other depicted embodiments in any combination. For example, any of the various components described herein and/or depicted in the figures may be combined, interchanged, or excluded from other embodiments.

The algorithms and equations herein are not limiting but instructive of the embodiment of the invention, and variations which are readily derived through programming or mathematical transformations which are standard or known to the appropriate art are not excluded by omission. Accordingly, it is intended that the appended claims are interpreted as covering all alterations and modifications as fall within the true spirit and scope of the invention in light of the prior art.

Additionally, although claims have been formulated in this application to particular combinations of elements, it should be understood that the scope of the disclosure of the present application also includes any single novel element or any novel combination of elements disclosed herein, either explicitly or implicitly, whether or not it relates to the same invention as presently claimed in any claim and whether or not it mitigates any or all of the same technical problems as does the present invention. The applicants hereby give notice that new claims may be formulated to such features and/or combinations of such features during the prosecution of the present application or of any further application derived therefrom.

I claim:

1. A bi-directional adaptive drug dispenser for managing divergence between pre-set regimen and actual performance, said dispenser being any of the set of a container or an attachment to a container used to store at least one dose comprising at least one unit of medication and said dispenser comprising:
 a storage volume;
 a battery compartment for a battery with power connections to power said bi-directional adaptive drug dispenser;
 an operations cap connected to said storage volume and the power connections that controls the filling and dispensing of any dose and unit of medication to or from said storage volume according to said pre-set regimen, further comprising:
  a visual display;
  at least two distinct lights on the distal face of the operations cap;

a control set of operational, input, and programming controls for the operations cap, further comprising:
a program button;
a clock button;
a quantity button;
an 'on/off' button;
and a dosing release button;
an operations set comprising any of a microprocessor, microcontroller or embedded controller, both static memory and dynamic memory, all used to store and run operational program(s) and data, and all connected through any of a bus, baseplane, and backplane to the control set which controls their activation and operation;
a distal filling door connecting said storage volume to the exterior of the container and controlled by said operations cap; and,
a bidirectional dose checking tunnel passing through said operations cap with a distal end connected to the distal filling door and a medial end connecting through a medial filling door to said storage volume, said bidirectional dose checking tunnel further comprising:
a distal counting sensor;
an identifying sensor;
a medial counting sensor; and,
a transfer means to move a unit of medication through the bidirectional dose checking tunnel and out either filling door thereof, said transfer means also connected to and controlled by said operations cap.

2. The bi-directional adaptive drug dispenser as in claim 1, wherein the transfer means comprises an electromagnetically-driven coil which is controlled by the operations cap, whose activation both transports any unit of medication within the bidirectional dose checking tunnel in a specific direction and is recorded as effecting that specific direction of transfer.

3. The bi-directional adaptive drug dispenser as in claim 2 wherein the bidirectional dose checking tunnel further comprises:
a diversion tube connecting through a diversion door that is also controlled by the operations cap, through which unacceptable units (whether or not of the correct medication) are diverted, said diversion door and diversion tube located in and connecting for and with said bidirectional dose checking tunnel both between the distal counting sensor and medial counting sensor and opposite the identifying sensor;
and said diversion tube is connected at its further end to a reject storage volume.

4. The bi-directional adaptive drug dispenser as in claim 3 wherein the operations cap further comprises a delivery element external to the distal filling door, said delivery element further comprising:
an external, distal delivery gate, controlled by the operations cap, openable through activation under proper conditions by a single press on the dosing release button;
a holding volume connecting said external, distal delivery gate and said distal filling door; and,
a medpresent sensor in the interior surface of the holding volume for detecting when a dose is currently, or is no longer, present in the delivery element, connecting to said operations cap.

5. The bi-directional adaptive drug dispenser as in claim 1 wherein the control set further comprises a reset button which when activated provides the capability to reset the operations cap to a predeterminable 'default' state stored in static memory.

6. The bi-directional adaptive drug dispenser as in claim 5, when the operations cap is not an integral part of but is an attachment to the container, wherein the operations cap further comprises at its medial interior end a sealed connection sensor operationally connected to said operations cap which registers that the operations cap is both correctly and connectedly affixed to the container.

7. The bi-directional adaptive drug dispenser as in claim 1 wherein said operations cap is programmed to effect delivery of a series of individual doses of one or more units of a medication according to a pre-set regimen, and testing and recording the actual performance and behavior, said programming further comprising the steps of:
activating a scheduled dose alert when the timer reaches the time set for the next dose;
sending the scheduled dose through the bidirectional dose checking tunnel from the storage volume;
closing the medial filling door and having the medial counting sensor increment the unit count as the unit passes distally over it and record that passage;
using the identifying sensor to compare the observed feature(s) of that unit against the pattern(s) stored in the static memory for the salient feature(s) of that class of unit, thus checking whether this is the right medication;
if the pattern is not matched, the exception for handling an incorrect medication is invoked that unit is discarded, and the steps of sending another unit from the storage volume into the bidirectional dose checking tunnel and checking whether this is the right medication are repeated;
if the pattern is matched, then the unit count is incremented and compared against the dose count to check whether the dosage quantity is right; and if multiple units are needed then the steps to send and check another unit are repeated, until the incremented unit count matches the dose count;
once the incremented count matches the dose count, the units in the bidirectional dose checking tunnel are passed over the distal counting sensor and the distal filling door is unlatched, so the dose (checked as to both identity of medication and count) is made available for pickup;
if the above steps have been performed independent of human effort then at this point an optional patient alert is sent to the user if he or she had not already received one, letting the patient (user) know that the dose is ready and available;
continuing to count the time through the period of any dosing window;
until either: (i) a user may, at any time during a dosing window, pick up the device and, through activating the control set seek to obtain the dose scheduled for that dosing window, and when the distal filling door is opened and the medication is removed by the user, the operations cap records that dose and time as having been taken and sets the timer counting towards the next scheduled dose release; or, (ii) if the dose is not removed before the dosing window is exceeded, then to any set of the prescriber and patient a late dose alert is sent and an exception to the treatment plan is logged into the static memory, and the operations cap latches the distal delivery door (any of the distal filling door and delivery gate), resets the time to the next dose, and sets the timer counting towards the next scheduled dose release.

8. The bi-directional adaptive drug dispenser as in claim 1 wherein said operations cap is programmed to effect delivery of a series of individual doses of one or more units of a medication according to a pre-set regimen and subject to a validation check, and testing and recording the actual performance and behavior, said programming further comprising the steps, at the invocation of a validation check, of:
  defaulting to a locked state for any of the latchable door-plus-sensor elements that would allow the removal of anything from the container;
  prompting the user to enter, using the control set, the validating authorization;
  upon receiving the response determining through the operations cap matching the provided input against the required pattern stored in the static memory, whether or not this specific taking of the medication is authorized;
  logging the attempt plus contextual information (time of day, location of container);
  If the user is not authorized, then the user is alerted to his invalidity, and an alert reporting the attempt is sent to the prescriber, treating the lack of authorization as an external constraint and, if the user fails to respond or otherwise does not request an exception to the constraint then the operations cap will reset the time for the next scheduled dose release (if the time has elapsed) or keep the timer counting towards the next scheduled dose release (if the time has not elapsed);
  but, if the user is authorized, then the operations cap will release the specified latch and thus release the dose; and set the timer counting towards the next scheduled dose release.

9. The bi-directional adaptive drug dispenser as in claim 1 wherein said operations cap is programmed to effect delivery of a series of individual doses of one or more units of a medication according to a pre-set regimen and for handling of an exception when a constraint of the treatment plan is reached, said programming further comprising the steps of: the operations cap using, each time that the dock matches up with a time within the limits of the dosing window as stored in the static memory that is, according to the treatment plan, when it is time for a dose to be taken, all data to evaluate whether any specific constraint that would prohibit, or constrain, the taking of that specific dose has be violated; if no constraint has been violated, then the dose is prepared for the user which if picked up on time results in the operation looping back to and timer counting towards the next scheduled dose release; but if a constraint has been violated, then: the operations cap will (a) log the constraint and its violation; (b) issue an alert to the user; and (c) issue an alert to the prescriber; if the user fails to respond or otherwise does not request an exception to the constraint, then the operations cap will reset the time for the next dose and set the times counting towards the next scheduled dose release; but, if the user does request an exception, then this request is sent to the prescriber, whose response or the lack thereof is logged and, if the exception is approved by the prescriber, the dose is prepared; while if the exception is not approved, it is not and the operations cap will reset the time for the next dose and set the timer counting towards the next scheduled dose release.

10. The bi-directional adaptive drug dispenser as in claim 1 further comprising any of the set of:
  a clock which is settable and programmable through said operations set;
  an electromagnetically-driven coil which is controlled by the operations cap, whose activation both transports any unit of medication within the bidirectional dose checking tunnel in a specific direction and is recorded as effecting that specific direction of transfer;
  a diversion tube connecting through a diversion door that is also controlled by the operations cap, through which unacceptable units are diverted, said diversion door and diversion tube located in and connecting for and with said bidirectional dose checking tunnel both between the distal counting sensor and medial counting sensor and opposite the identifying sensor; and said diversion tube is connected at its further end to a reject storage volume;
  an external, distal delivery gate, controlled by the operations cap, openable through activation under proper conditions by a single press on the dosing release button; a holding volume connecting said external, distal delivery gate holding volume for detecting when a dose is currently, or is no longer, present in the delivery element, connecting to said operations cap;
  a reset button which when activated provides the capability to reset the operations cap to a predeterminable 'default' state stored in static memory;
  and, for when the operations cap is not an integral part of but is an attachment to the container, wherein the operations cap further comprises at its medial interior end a sealed connection sensor operationally connected to said operations cap which registers that the operations cap is both correctly and connectedly affixed to the container.

11. The bi-directional adaptive drug dispenser as in claim 10 further comprising:
  a speaker for audio output;
  a microphone for audio input; and,
  a speech synthesizer.

12. The bi-directional adaptive drug dispenser as in claim 10 wherein the operations cap further comprises and controls a panic button which is settable and programmable through said operations set, that requires only a single, but sustained press to activate, that upon activation uses the GPS to determine the physical location of the user and sends this location data, an emergency call-out to local emergency services; and the time of activation of the panic button.

13. The bi-directional adaptive drug dispenser as in claim 1, further comprising a radio sensor configured to detect and track the presence and removal of individual units which have any of a radio frequency identification chip and like short-range, even in-body wireless connections, where the absence of the signal when the radio frequency identification chip is shielded from detection within the human alimentary system or effecting burst when a reactive sensor encounters a triggering substance indicates that the bearing dosage has in fact entered the patient's digestive system.

14. A bi-directional adaptive drug dispenser for managing divergence between pre-set regimen and actual performance, said dispenser being any of the set of a container or an attachment to a container used to store at least one dose comprising at least one unit of medication and said dispenser comprising:
  a storage volume;
  a battery compartment for a battery with power connections to power said bi-directional adaptive drug dispenser;
  an operations cap connected to said storage volume and the power connections that controls the filling and dispensing of any dose and unit of medication to or from said storage volume according to said pre-set regimen, further comprising:
    a visual display;
    at least two distinct lights on the distal face of the operations cap;
    a control set of operational, input, and programming controls for the operations cap, further comprising:
      a program button;
      a clock button;

a quantity button;
an 'on/off' button;
and a dosing release button;
an operations set comprising any of a microprocessor, microcontroller or embedded controller, both static memory and dynamic memory, all used to store and run operational program(s) and data, and all connected through any of a bus, baseplane, and backplane to the control set which controls their activation and operation;
a distal filling door connecting said storage volume to the exterior of the container and controlled by said operations cap; and,
a first bidirectional dose checking tunnel passing through said operations cap with a distal end connected to the distal filling door and a medial end connecting through a medial filling door to said storage volume, said first bidirectional dose checking tunnel further comprising:
a first distal counting sensor;
an first identifying sensor;
a medial first counting sensor; and,
a first transfer means to move a unit of medication through the first bidirectional dose checking tunnel and out either filling door thereof, said first transfer means also connected to and controlled by said operations cap;
a second bidirectional dose checking tunnel, controlled by the operations cap, and connected to a separate location of the storage volume opposite the medial filling door for delivery of any set of units of medication from said storage volume to the exterior of the container, said second bidirectional dose checking tunnel further comprising:
a medial second filling door connecting to the interior of the storage volume and separating that from the interior of the second bidirectional dose checking tunnel;
a medial second counting sensor;
a second identifying sensor;
a distal second counting sensor;
a distal second filling door connecting to a delivery element; and,
a second transfer means to move a unit of medication through the second bidirectional dose checking tunnel; and,
having said delivery element further comprise a holding volume, a delivery gate at and separating the interior of the holding volume from the exterior of the container on the opposite side from the distal second filling door, said delivery gate being connected to and controlled by the operations cap and through which medication is delivered to the user.

15. The bi-directional adaptive drug dispenser as in claim 14 wherein each dose checking tunnel further comprises:
a diversion tube connecting through a diversion door that is also controlled by the operations cap, through which unacceptable units (whether or not of the correct medication) are diverted, said diversion door and diversion tube located in and connecting for and with said dose checking tunnel both between the distal counting sensor and medial counting sensor and opposite the identifying sensor;
and said diversion tube is connected at its further end to a reject storage volume.

16. The bi-directional adaptive drug dispenser as in claim 15 further comprising a medpresent sensor connected to said operations cap and located within the interior of and preferably at the interior surface of the holding volume, for detecting the presence of a pill within the holding volume.

17. The bi-directional adaptive drug dispenser as in claim 16 further comprising at the exterior of the container and operationally connected to the operations cap, a return button, connected to said operations cap that will effect movement of the contents of the delivery element back through the second bidirectional dose checking tunnel back into any of the set of the storage volume and the reject storage volume.

18. A bi-directional adaptive drug dispenser for managing divergence between pre-set regimen and actual performance, said dispenser being any of the set of a container or an attachment to a container used to store at least one dose comprising at least one unit of medication and said dispenser comprising:
a storage volume;
a battery compartment for a battery with power connections to power said bi-directional adaptive drug dispenser;
an operations cap connected to said storage volume and the power connections that controls the filling and dispensing of any dose and unit of medication to or from said storage volume according to said pre-set regimen, further comprising:
a visual display;
at least two distinct lights on the distal face of the operations cap;
a control set of operational, input, and programming controls for the operations cap, further comprising:
a program button;
a clock button;
a quantity button;
an 'on/off' button;
and a dosing release button;
an operations set comprising any of a microprocessor, microcontroller or embedded controller, both static memory and dynamic memory, all used to store and run operational program(s) and data, and all connected through any of a bus, baseplane, and backplane to the control set which controls their activation and operation;
a distal filling door connecting said storage volume to the exterior of the container and controlled by said operations cap; and,
a bidirectional dose checking tunnel passing through said operations cap with a distal end connected to the distal filling door and a medial end connecting through a medial filling door to said storage volume, said bidirectional dose checking tunnel further comprising:
a distal counting sensor;
an identifying sensor;
a medial counting sensor; and,
a transfer means to move a unit of medication through the bidirectional dose checking tunnel and out either filling door thereof, said transfer means also connected to and controlled by said operations cap;
a clock which is settable and programmable through said operations set;
an electromagnetically-driven coil which is controlled by the operations cap, whose activation both transports any unit of medication within the dose checking tunnel in a specific direction and is recorded as effecting that specific direction of transfer;
a diversion tube connecting through a diversion door that is also controlled by the operations cap, through which unacceptable units are diverted, said diversion door and diversion tube located in and connecting for and with said bidirectional dose checking tunnel both between the distal counting sensor and medial counting sensor and opposite the identifying sensor; and said diversion tube is connected at its further end to a reject storage volume;

an external, distal delivery gate, controlled by the operations cap, openable through activation under proper conditions by a single press on the dosing release button; a holding volume connecting said external, distal delivery gate and said distal filling door; and a medpresent sensor in the interior surface of the holding volume for detecting when a dose is currently, or is no longer, present in the delivery element, connecting to said operations cap;

a reset button which when activated provides the capability to reset the operations cap to a predeterminable 'default' state stored in static memory;

and, for when the operations cap is not an integral part of but is an attachment to the container, wherein the operations cap further comprises at its medial interior end a sealed connection sensor operationally connected to said operations cap which registers that the operations cap is both correctly and connectedly affixed to the container;

a remote link controlled by and connecting said operations cap through any set of a wire plug for a communications wire or a wireless communications device to any set of external computational and communication assets;

a panic button which is settable and programmable through said operations set, that requires only a single, but sustained press to activate, that upon activation uses the GPS to determine the physical location of the user and sends this location data, an emergency call-out to local emergency services; and the time of activation of the panic button;

an embedded application programming interface capable of operating, programming, and reprogramming the device through these additional devices by standard remote linkages;

an audio element controlled by said operations cap and further comprising:
a speaker for audio output; and
a microphone for audio input;
and,
a speech synthesizer.

19. The bi-directional adaptive drug dispenser as in claim 18 further comprising at least one placeable and removable insert specifically sized and shaped for the intended and particular medication unit, which insert fitted inside the filling bidirectional dose checking tunnel, and so configured as to allow unobstructed sensing of each of the medial counting sensor, identifying sensor, and distal counting sensor, and also having its interior wall a featureless, smooth, matte black colored, and low reflection material.

* * * * *